United States Patent [19]

Nannini et al.

[11] 4,388,314

[45] * Jun. 14, 1983

[54] HETEROMONOCYCLIC AND HETEROBICYCLIC DERIVATIVES OF UNSATURATED 7-ACYLAMIDO-3-CEPHEM-4-CARBOXYLIC ACID

[75] Inventors: Giuliano Nannini; Ettore Perrone, both of Bresso; Dino Severino, Vedasco di Stresa; Giuseppe Meinardi, Milan; Gisella Monti, Milan; Alberta Bianchi, Milan; Angelo Forgione, Milan; Carlo Confalonieri, Cusano Milanino, all of Italy

[73] Assignee: Farmitalia Carlo Erba S.p.A., Milan, Italy

[ * ] Notice: The portion of the term of this patent subsequent to May 15, 1996, has been disclaimed.

[21] Appl. No.: 295,074

[22] Filed: Aug. 21, 1981

Related U.S. Application Data

[60] Continuation of Ser. No. 134,788, Mar. 28, 1980, abandoned, which is a continuation of Ser. No. 47,893, Jun. 12, 1979, abandoned, which is a division of Ser. No. 868,665, Jan. 11, 1978, Pat. No. 4,172,892.

[30] Foreign Application Priority Data

Feb. 11, 1977 [IT]  Italy .............................. 20173 A/77

[51] Int. Cl.$^3$ ................. C07D 501/36; A61K 31/545
[52] U.S. Cl. ...................................... 424/246; 544/26
[58] Field of Search ....................... 544/16, 26, 27, 21; 424/246

[56] References Cited

U.S. PATENT DOCUMENTS

| | | | |
|---|---|---|---|
| 4,057,631 | 11/1977 | Berges | 544/26 |
| 4,079,134 | 3/1978 | Berges | 544/26 |
| 4,154,830 | 5/1979 | Nannini et al. | 544/26 |
| 4,172,892 | 10/1979 | Nannini et al. | 424/246 |

*Primary Examiner*—Nicholas S. Rizzo
*Attorney, Agent, or Firm*—Murray and Whisenhunt

[57] ABSTRACT

Heteromonocyclic and heterobicyclic derivatives of unsaturated 7-ayclamide-3-cephem-4-carboxylic acid are disclosed, and process for preparing same. These compounds are suitable for treating infections caused by Gram-positive and Gram-negative microorganisms.

9 Claims, No Drawings

HETEROMONOCYCLIC AND HETEROBICYCLIC DERIVATIVES OF UNSATURATED 7-ACYLAMIDO-3-CEPHEM-4-CARBOXYLIC ACID

This is a continuation application of Ser. No. 134,788, filed Mar. 28, 1980 now abandoned, which was a continuation of Ser. No. 47,893, filed June 12, 1979 now abandoned, which was a division of Ser. No. 868,665, filed Jan. 11, 1978 now U.S. Pat. No. 4,172,892.

The present invention relates to heteromonocyclic and heterobicyclic derivatives of unsaturated 7-acylamido-3-cephem-4-carboxylic acid, to a process for their preparation and to pharmaceutical and veterinary compositions containing them.

The compounds of the invention have the following formula (I)

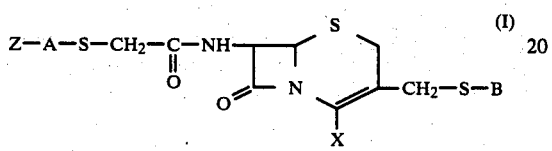

wherein

Z is cyano, carbamoyl or —COOR, wherein R is a hydrogen or $C_1$-$C_6$ alkyl;

A is a $C_2$-$C_6$ branched or unbranched unsaturated aliphatic hydrocarbon radical, which is unsubstituted or substituted by one or more substituents selected from the group consisting of (a) hydroxy; (b) halogen; (c) cyano; (d) —COOR, wherein R is as defined above; (e) —COR, wherein R is as defined above; (f) $R_1$—$SO_2$—, wherein $R_1$ is $C_1$-$C_6$ alkyl; (g)

wherein each of $R_2$ and $R_3$, which may be the same or different, is hydrogen or $C_1$-$C_6$ alkyl, or $R_2$ and $R_3$, taken together with the nitrogen atom, form a pentatomic or hexatomic, saturated or unsaturated, heteromonocyclic ring optionally containing another heteroatom selected from the group consisting of N, S and O; (h)

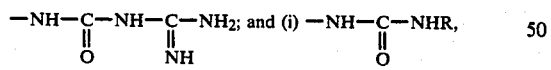

wherein R is as defined above;

X is a free or esterified carboxy group;

B is (1) a tetrazolyl radical, substituted by (a') $C_2$-$C_4$ alkyl; (b') $C_2$-$C_4$ alkenyl; (c') —$CH_2CN$; (d')

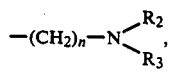

wherein n is zero or an integer of 1 to 3 and $R_2$ and $R_3$ are as defined above; (e') —$(CH_2)_n$—COOR, wherein n and R are as defined above; (f') —CH=CH—COOR, wherein R is as defined above; (g') —$(CH_2)_n$—CO—$NH_2$, wherein n is as defined above; (h') —$CH_2$—CH=NO—$CH_2COOR$, wherein R is as defined above; (i') —CH=CH—$CONH_2$; (l') —$(CH_2)_n$—$SO_3H$, wherein n is as defined above; (m') —CH=CH—$SO_3H$; (2) a thiadiazolyl radical, substituted by (a") $C_1$-$C_4$ alkyl; (b") cyano; (c") hydroxy; (d") $C_1$-$C_4$ alkoxy; (e") —$CH_2CN$; (f") carbamoyl; (g") —SR, wherein R is as defined above; (h") —$SO_2R$, wherein R is as defined above; (i") $R_1$—$SO_2$—NH—, wherein $R_1$ is as defined above; (l")

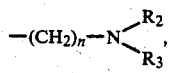

wherein n, $R_2$ and $R_3$ are as defined above; (m") —$(CH_2)_n$—COOR, wherein n and R are as defined above; (n") —CH=CH—COOR, wherein R is as defined above; (o") —NH—$CONH_2$; (p") —$CH_2$—CO—$NH_2$; (q") —NH—$CH_2$—COOR, wherein R is as defined above; (r") —NH—CO—$(CH_2)_n$—COOR, wherein n and R are as defined above; (s") —NH—CH=CH—COOR, wherein R is as defined above; (t") —CH=CH—$CONH_2$; (u") —$(CH_2)_n$—$SO_3H$, wherein n is as defined above; (v") —CH=CH—$SO_3H$; (z") —NH—CO—CH=CH—COOR, wherein R is as defined above; (3) a heterobicyclic ring containing at least two double bonds, wherein each of the condensed heteromonocyclic rings, being the same or different, is a pentatomic or hexatomic heteromonocyclic ring containing at least a heteroatom selected from the group consisting of N, S and O, being the heterobicyclic ring unsubstituted or substituted by one or more substituents selected from the group consisting of (a''') hydroxy; (b''') cyano; (c''') —SH; (d''') halogen; (e''') aliphatic $C_1$-$C_6$ acyl; (f''') —$CH_2CN$; (h''')

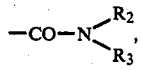

wherein $R_2$ and $R_3$ are as defined above; (g''') —COOR, wherein R is as defined above; (h''') amino, unsubstituted or substituted by a aliphatic $C_1$-$C_6$ acyl group or by a —$(CH_2)_n$—COOR group, wherein n and R are as defined above; (i''') $C_1$-$C_6$ alkyl unsubstituted or substituted by one or more substituents selected from the group consisting of hydroxy and halogen; (l''')

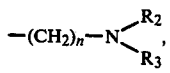

wherein n, $R_2$ and $R_3$ are as defined above; (m''') —$SR_1$, wherein $R_1$ is as defined above; (n''') —$SO_2R_1$, wherein $R_1$ is as defined above; (o''') —S—$CH_2$—CN; (p''') —S—$CH_2$—CO—$NH_2$; and (q''') —$(S)_{n1}$—$CH_2$—COOR, wherein $n_1$ is zero or 1 and R is as defined above.

The present invention also includes within its scope the pharmaceutically and veterinarily acceptable salts as well as all the possible cis- and trans- isomers and the stereoisomers of formula (I) and their mixtures, the metabolites provided with antibacterial activity and the metabolic precursors of the compounds of formula (I).

The alkyl, alkenyl, alkoxy and aliphatic acyl groups may be branched or straight chain.

When X is an esterified carboxy group, it is preferably a group of formula —COOM, wherein M is one of the radicals

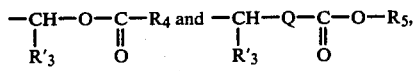

wherein $R_3'$ is hydrogen or $C_1$-$C_6$ alkyl, Q is —O— or —NH—, $R_4$ is an alkyl group (e.g., $C_1$-$C_6$ alkyl) or a basic group, in particular an alkyl (e.g. $C_1$-$C_6$ alkyl) or aralkyl (e.g. benzyl) group substituted by at least an amino group, which in turn, may be unsubstituted or substituted, e.g., $R_4$ is alkyl—NH—$CH_3$, aralkyl—NH—$CH_3$,

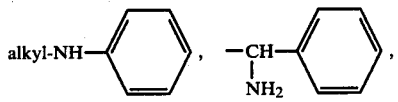

—$CH_2$—$NH_2$, $R_5$ is an alkyl group, in particular a $C_1$-$C_6$ alkyl group, e.g., methyl, propyl, isopropyl; an aryl group, in particular phenyl; a cycloalkyl group, in particular cyclopentyl, cyclohexyl and cycloheptyl; a heteromonocyclic ring, e.g., pyridyl; a heterobicyclic ring, e.g., indanyl; an aralkyl group, e.g., benzyl. When B is a heterobicyclic ring it is preferably selected from the group consisting of tetrazolopyridazinyl, tetrazolopyrimidinyl, tetrazolopyrazinyl, furopyridazinyl, thiazolopyridazinyl, thiadiazolopyridazinyl, thienopyridazinyl, tetrazolotriazinyl and tetrazolopyridyl, optionally substituted as reported above.

Z is preferably cyano or carbamoyl. X is preferably a free or salified carboxy group.

Particularly preferred compounds are the cis-isomers of the compounds wherein A is an aliphatic hydrocarbon radical containing at least one double bond.

The unsaturated aliphatic hydrocarbon radical A preferably contains 2 to 4 carbon atoms; in particular it may be —CH=CH— or —C≡C—, preferably cis—CH=CH—. The pharmaceutically and veterinarily acceptable salts of the compounds of formula (I) are those either with inorganic acids, such as hydrochloric and sulphuric acid, or with organic acids, such as citric, tartaric, malic, maleic, mandelic, fumaric and methanesulphonic acid, or with inorganic bases, such as sodium, potassium, calcium or aluminium hydroxides and alkaline or alkaline-earth carbonates or bicarbonates, or with organic bases, such as organic amines, e.g., lysine, triethylamine, procaine, dibenzylamine, N-benzyl-$\beta$-phenetylamine, N,N'-dibenzyl-ethylenediamine, dehydroabietilamine, N-ethylpiperidine, diethanolamine, N-methylglucamine, tris-hydroxymethyl-aminomethane and the like.

Also the internal salts (i.e. zwitterions) are included in the scope of the invention.

Preferred salts are those of the compounds of the invention, wherein X is a free carboxy group, with inorganic or organic bases, e.g., those mentioned above.

Particularly preferred compounds are those of formula (I) wherein Z is cyano or carbamoyl, A is cis-—CH=CH— or —C≡C—, X is a free or salified carboxy group, B is (1) a tetrazolyl radical, substituted by $C_2$-$C_4$ alkyl, $C_2$-$C_4$ alkenyl, —$(CH_2)_n$—COOR, wherein n and R are as defined above, —CH=CH—COOR, wherein R is as defined above, —$(CH_2)_n$—$SO_3H$, wherein n is as defined above, or —CH=CH—$SO_3H$, (2) a thiadiazolyl radical, substituted by $C_1$-$C_4$ alkyl,

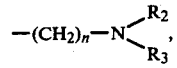

wherein n, $R_2$ and $R_3$ are as defined above, —$(CH_2)_n$—COOR, wherein n and R are as defined above, —CH=CH—COOR, wherein R is as defined above, —NH—$CONH_2$, —$CH_2$—$CONH_2$, —NH—$CH_2$—COOR, wherein R is as defined above, —NH—CO—$(CH_2)_n$—COOR, wherein n and R are as defined above, or —$(CH_2)_n$—$SO_3H$, wherein n is as defined above, or (3) a heterobicyclic ring, selected from the group consisting of tetrazolopyridazinyl, tetrazolopyrazinyl, thiadiazolopyridazinyl, and tetrazolotriazinyl, optionally substituted by hydroxy, —SH,

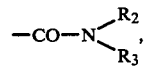

wherein $R_2$ and $R_3$ are as defined above, —COOR, wherein R is as defined above, —$SR_1$, wherein $R_1$ is as defined above, —S—$CH_2$—CO—$NH_2$, —$(S)_{n1}$—$CH_2$—COOR, wherein $n_1$ is zero or 1 and R is as defined above, or amino, unsubstituted or substituted by a $C_1$-$C_6$ aliphatic acyl group or by a —$(CH_2)_n$—COOR group, wherein n and R are as defined above; and the pharmaceutically and veterinarily acceptable salts thereof.

Specific examples of the compounds of the invention are the following:

(1) 7-[$\beta$-cyano-ethylene(cis)-thio-acetamido]-3-[(1-ethyl-1,2,3,4-tetrazol-5-yl)-thiomethyl]-3-cephem-4-carboxylic acid;

(2) 7-[$\beta$-cyano-ethylene(cis)-thio-acetamido]-3-[(1-(2)-propenyl-1,2,3,4-tetrazol-5-yl)-thiomethyl]-3-cephem-4-carboxylic acid;

(3) 7-[$\beta$-cyano-ethylene(cis)-thio-acetamido]-(3-[(1-(1)-propenyl-1,2,3,4-tetrazol-5-yl)-thiomethyl]-3-cephem-4-carboxylic acid;

(4) 7-[$\beta$-cyano-ethylene(cis)-thio-acetamido]-3-[(1-carboxymethyl-1,2,3,4-tetrazol-5-yl)-thiomethyl]-3-cephem-4-carboxylic acid;

(5) 7-[$\beta$-cyano-ethylene(cis)-thio-acetamido]-3-[(1-$\beta$-carboxyethyl-1,2,3,4-tetrazol-5-yl)-thiomethyl]-3-cephem-4-carboxylic acid;

(6) 7-[$\beta$-cyano-ethylene(cis)-thio-acetamido]-3-[(1-$\gamma$-carboxypropyl-1,2,3,4-tetrazol-5-yl)-thiomethyl]-3-cephem-4-carboxylic acid;

(7) 7-[$\beta$-cyano-ethylene(cis)-thio-acetamido]-3-[(1-$\beta$-carboxyethylene-1,2,3,4-tetrazol-5-yl)-thiomethyl]-3-cephem-4-carboxylic acid;

(8) 7-[$\beta$-cyano-ethylene(cis)-thio-acetamido]-3-[(1-carboxymethyl-oxy-iminomethyl-1,2,3,4-tetrazol-5-yl)-thiomethyl]-3-cephem-4-carboxylic acid;

(9) 7-[$\beta$-cyano-ethylene(cis)-thio-acetamido]-3-[(1-carboxamidomethyl-1,2,3,4-tetrazol-5-yl)-thiomethyl]-3-cephem-4-carboxylic acid;

(10) 7-[$\beta$-cyano-ethylene(cis)-thio-acetamido]-3-[(1-$\beta$-carboxamidoethyl-1,2,3,4-tetrazol-5-yl)-thiomethyl]-3-cephem-4-carboxylic acid;

(11) 7-[β-cyano-ethylene(cis)-thio-acetamido]-3-[(1-sulfomethyl-1,2,3,4-tetrazol-5-yl)-thiomethyl]-3-cefem-4-carboxylic acid;

(12) 7-[β-cyano-ethylene(cis)-thio-acetamido]-3-[(1-β-sulfoethyl-1,2,3,4-tetrazol-5-yl)-thiomethyl]-3-cephem-4-carboxylic acid;

(13) 7-[β-cyano-ethylene(cis)-thio-acetamido]-3-[(1-β-sulfoethylene-1,2,3,4-tetrazol-5-yl)-thiomethyl]-3-cephem-4-carboxylic acid;

(14) 7-[β-cyano-ethylene(cis)-thio-acetamido]-3-[(1-β-dimethylaminoethyl-tetrazol-5-yl)-thiomethyl]-3-cephem-4-carboxylic acid;

(15) 7-[β-cyano-ethylene(cis)-thio-acetamido]-3-[(5-amino-1,3,4-thiadiazol-2-yl)-thiomethyl]-3-cephem-4-carboxylic acid;

(16) 7-[β-cyano-ethylene(cis)-thio-acetamido]-3-[(5-carboxymethyl-amino-1,3,4-thiadiazol-2-yl)-thiomethyl]-3-cephem-4-carboxylic acid;

(17) 7-[β-cyano-ethylene(cis)-thio-acetamido]-3-[(5-carboxymethyl-1,3,4-thiadiazol-2-yl)-thiomethyl]-3-cephem-4-carboxylic acid;

(18) 7-[β-cyano-ethylene(cis)-thio-acetamido]-3-[(5-succinamido-1,3,4-thiadiazol-2-yl)-thiomethyl]-3-cephem-4-carboxylic acid;

(19) 7-[β-cyano-ethylene(cis)-thio-acetamido]-3-[(5-maleamido-1,3,4-thiadiazol-2-yl)-thiomethyl]-3-cephem-4-carboxylic acid;

(20) 7-[β-cyano-ethylene(cis)-thio-acetamido]-3-[(5-β-carboxyethylene-1,3,4-thiadiazol-2-yl)-thiomethyl]-3-cephem-4-carboxylic acid;

(21) 7-[β-cyano-ethylene(cis)-thio-acetamido]-3-[(5-β-carboxyethyl-1,3,4-thiadiazol-2-yl)-thiomethyl]-3-cephem-4-carboxylic acid;

(22) 7-[β-cyano-ethylene(cis)-thio-acetamido]-3-[(5-ureido-1,3,4-thiadiazol-2-yl)-thiomethyl]-3-cephem-4-carboxylic acid;

(23) 7-(cyano-ethynylene-thio-acetamido)-3-[(1-carboxymethyl-1,2,3,4-tetrazol-5-yl)-thiomethyl]-3-cephem-4-carboxylic acid;

(24) 7-(cyano-ethynylene-thio-acetamido)-3-[(1-β-carboxyethyl-1,2,3,4-tetrazol-5-yl)-thiomethyl]-3-cephem-4-carboxylic acid;

(25) 7-(cyano-ethynylene-thio-acetamido)-3-[(1-sulfomethyl-1,2,3,4-tetrazol-5-yl)-thiomethyl]-3-cephem-4-carboxylic acid;

(26) 7-[β-cyano-ethylene(cis)-thio-acetamido]-3-[(tetrazolo[1,5-b]pyridazin-6-yl)-thiomethyl]-3-cephem-4-carboxylic acid;

(27) 7-[β-cyano-ethylene(cis)-thio-acetamido]-3-[(tetrazolo[1,5-b]pyridazin-8-amino-6-yl)-thiomethyl]-3-cephem-4-carboxylic acid;

(28) 7-[β-cyano-ethylene(cis)-thio-acetamido]-3-{[tetrazolo[1,5-b]pyridazin-8-N(carboxymethyl)-6-yl]-thiomethyl}-3-cephem-4-carboxylic acid;

(29) 7-[β-cyano-ethylene(cis)-thio-acetamido]-3-[(tetrazolo[1,5-b]pyridazin-8-carboxy-6-yl)-thiomethyl]-3-cephem-4-carboxylic acid;

(30) 7-[β-cyano-ethylene(cis)-thio-acetamido]-3-[(tetrazolo[1,5-b]pyridazin-8-hydroxy-6-yl)-thiomethyl]-3-cephem-4-carboxylic acid;

(31) 7-[β-cyano-ethylene(cis)-thio-acetamido]-3-[(1,2,5-thiadiazolo[3,4-d]pyridazin-4-yl)-thiomethyl]-3-cephem-4-carboxylic acid;

(32) 7-[β-cyano-ethylene(cis)-thio-acetamido]-3-[(tetrazolo[4,5-a]pyrazin-6-yl)-thiomethyl]-3-cephem-4-carboxylic acid;

(33) 7-[β-cyano-ethylene(cis)-thio-acetamido]-3-[(tetrazolo[4,5-a]pyrazin-8-amino-6-yl)-thiomethyl]-3-cephem-4-carboxylic acid;

(34) 7-[β-cyano-ethylene(cis)-thio-acetamido]-3-[(tetrazolo[1,5-b]pyridazin-8-carboxymethyl-6-yl)-thiomethyl]-3-cephem-4-carboxylic acid;

(35) 7-[β-cyano-ethylene(cis)-thio-acetamido]-3-[(tetrazolo[1,5-b]pyridazin-7-amino-8-yl)-thiomethyl]-3-cephem-4-carboxylic acid;

(36) 7-[β-carboxamido-ethylene(cis)-thio-acetamido]-3-[(1-carboxymethyl-1,2,3,4-tetrazol-5-yl)-thiomethyl]-3-cephem-4-carboxylic acid;

(37) 7-[β-carboxamido-ethylene(cis)-thio-acetamido]-3-[(1-β-carboxyethyl-1,2,3,4-tetrazol-5-yl)-thiomethyl]-3-cephem-4-carboxylic acid;

(38) 7-[β-carboxamido-ethylene(cis)-thio-acetamido]-3-[(1-β-carboxyethylene-1,2,3,4-tetrazol-5-yl)-thiomethyl]-3-cephem-4-carboxylic acid;

(39) 7-[β-carboxamido-ethylene(cis)-thio-acetamido]-3-[(1-β-sulfoethylene-1,2,3,4-tetrazol-5-yl)-thiomethyl]-3-cephem-4-carboxylic acid;

(40) 7-[β-carboxamido-ethylene(cis)-thio-acetamido]-3-[(1-(1)-propenyl-1,2,3,4-tetrazol-5-yl)-thiomethyl]-3-cephem-4-carboxylic acid;

(41) 7-[β-carboxamido-ethylene(cis)-thio-acetamido]-3-[(1-ethyl-1,2,3,4-tetrazol-5-yl)-thiomethyl]-3-cephem-4-carboxylic acid;

(42) 7-[β-carboxamido-ethylene(cis)-thio-acetamido]-3-[(tetrazolo[1,5-b]pyridazin-6-yl)-thiomethyl]-3-cephem-4-carboxylic acid;

(43) 7-[β-carboxamido-ethylene(cis)-thio-acetamido]-3-[(tetrazolo[1,5-b]pyridazin-8-amino-6-yl)-thiomethyl]-3-cephem-4-carboxylic acid;

(44) 7-[β-carboxamido-ethylene(cis)-thio-acetamido]-3-[(tetrazolo[1,5-b]pyridazin-7-amino-8-yl)-thiomethyl]-3-cephem-4-carboxylic acid;

(45) 7-[β-cyano-ethylene(cis)-thio-acetamido]-3-[(tetrazolo[1,5-b]pyridazin-7,8-diamino-6-yl)-thiomethyl]-3-cephem-4-carboxylic acid;

(46) 7-[β-carboxamido-ethylene(cis)-thio-acetamido]-3-[(tetrazolo[1,5-b]pyridazin-7,8-diamino-6-yl)-thiomethyl]-3-cephem-4-carboxylic acid;

(47) 7-(cyano-ethynylene-thio-acetamido)-3-[(tetrazolo[1,5-b]pyridazin-6-yl)-thiomethyl]-3-cephem-4-carboxylic acid;

(48) 7-(cyano-ethynylene-thio-acetamido)-3-[(tetrazolo[1,5-b]pyridazin-8-amino-6-yl)-thiomethyl]-3-cephem-4-carboxylic acid;

(49) 7-(carboxamido-ethynylene-thio-acetamido)-3-[(tetrazolo[1,5-b]pyridazin-6-yl)-thiomethyl]-3-cephem-4-carboxylic acid;

(50) 7-(carboxamido-ethynylene-thio-acetamido)-3-[(tetrazolo[1,5-b]pyridazin-8-amino-6-yl)-thiomethyl]-3-cephem-4-carboxylic acid;

(51) 7-[β-carboxy-ethylene(cis)-thio-acetamido]-3-[(tetrazolo[1,5-b]pyridazin-6-yl)-thiomethyl]-3-cephem-4-carboxylic acid;

(52) 7-[β-carboxy-ethylene(cis)-thio-acetamido]-3-[(tetrazolo[1,5-b]pyridazin-8-amino-6-yl)-thiomethyl]-3-cephem-4-carboxylic acid.

The structural formulae of the above-numbered compounds, indicated according to their progressive number, are reported in the following Table.

TABLE

| Compound | Z | A | X | B |
|---|---|---|---|---|
| 1 | NC— | —CH=CH— | —COOH | tetrazole-N-C₂H₅ |
| 2 | NC— | —CH=CH— | —COOH | tetrazole-N-CH₂—CH=CH₂ |
| 3 | NC— | —CH=CH— | —COOH | tetrazole-N-CH=CH—CH₃ |
| 4 | NC— | —CH=CH— | —COOH | tetrazole-N-CH₂COOH |
| 5 | NC— | —CH=CH— | —COOH | tetrazole-N-(CH₂)₂—COOH |
| 6 | NC— | —CH=CH— | —COOH | tetrazole-N-(CH₂)₃—COOH |
| 7 | NC— | —CH=CH— | —COOH | tetrazole-N-CH=CH—COOH |
| 8 | NC— | —CH=CH— | —COOH | tetrazole-N-CH=NOCH₂—COOH |
| 9 | NC— | —CH=CH— | —COOH | tetrazole-N-CH₂CONH₂ |
| 10 | NC— | —CH=CH— | —COOH | tetrazole-N-CH₂CH₂CONH₂ |
| 11 | NC— | —CH=CH— | —COOH | tetrazole-N-CH₂SO₃H |

TABLE-continued
| Compound | Z | A | X | B |
|---|---|---|---|---|
| 12 | NC— | —CH=CH— | —COOH | 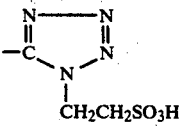 |
| 13 | NC— | —CH=CH— | —COOH | 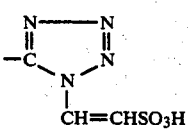 |
| 14 | NC— | —CH=CH— | —COOH | 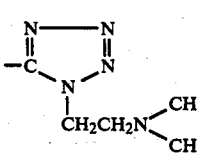 |
| 15 | NC— | —CH=CH— | —COOH | 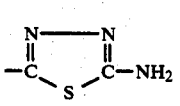 |
| 16 | NC— | —CH=CH— | —COOH | 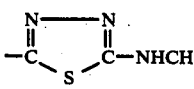 |
| 17 | NC— | —CH=CH— | —COOH | 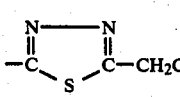 |
| 18 | NC— | —CH=CH— | —COOH | 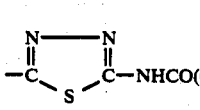 |
| 19 | NC— | —CH=CH— | —COOH | 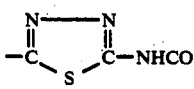 |
| 20 | NC— | —CH=CH— | —COOH | 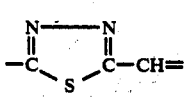 |
| 21 | NC— | —CH=CH— | —COOH | 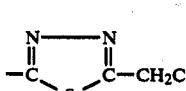 |
| 22 | NC— | —CH=CH— | —COOH | 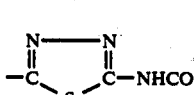 |
| 23 | NC— | —C≡C— | —COOH | 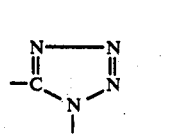 |
| 24 | NC— | —C≡C— | —COOH | 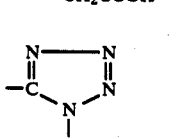 |

TABLE-continued

| Compound | Z | A | X | B |
|---|---|---|---|---|
| 25 | NC— | —C≡C— | —COOH | tetrazole with CH₂SO₃H substituent |
| 26 | NC— | —CH=CH— | —COOH | tetrazolo[1,5-b]pyridazine |
| 27 | NC— | —CH=CH— | —COOH | tetrazolo[1,5-b]pyridazine with NH₂ |
| 28 | NC— | —CH=CH— | —COOH | tetrazolo[1,5-b]pyridazine with NHCH₂COOH |
| 29 | NC— | —CH=CH— | —COOH | tetrazolo[1,5-b]pyridazine with COOH |
| 30 | NC— | —CH=CH— | —COOH | tetrazolo[1,5-b]pyridazine with OH |
| 31 | NC— | —CH=CH— | —COOH | [1,2,5]thiadiazolo-pyridazine |
| 32 | NC— | —CH=CH— | —COOH | tetrazolo-pyrazine |
| 33 | NC— | —CH=CH— | —COOH | tetrazolo-pyrazine with NH₂ |
| 34 | NC— | —CH=CH— | —COOH | tetrazolo[1,5-b]pyridazine with CH₂COOH |

TABLE-continued

| Compound | Z | A | X | B |
|---|---|---|---|---|
| 35 | NC— | —CH=CH— | —COOH | 4-amino-6-methyl-tetrazolo[1,5-b]pyridazine group |
| 36 | H$_2$NCO— | —CH=CH— | —COOH | tetrazol-5-yl with N-CH$_2$COOH |
| 37 | H$_2$NCO— | —CH=CH— | —COOH | tetrazol-5-yl with N-CH$_2$CH$_2$COOH |
| 38 | H$_2$NCO— | —CH=CH— | —COOH | tetrazol-5-yl with N-CH=CH-COOH |
| 39 | H$_2$NCO— | —CH=CH— | —COOH | tetrazol-5-yl with N-CH=CH-SO$_3$H |
| 40 | H$_2$NCO— | —CH=CH— | —COOH | tetrazol-5-yl with N-CH=CH-CH$_3$ |
| 41 | H$_2$NCO— | —CH=CH— | —COOH | tetrazol-5-yl with N-C$_2$H$_5$ |
| 42 | H$_2$NCO— | —CH=CH— | —COOH | 6-methyl-tetrazolo[1,5-b]pyridazine group |
| 43 | H$_2$NCO— | —CH=CH— | —COOH | 4-amino-6-methyl-tetrazolo[1,5-b]pyridazine group |
| 44 | H$_2$NCO— | —CH=CH— | —COOH | 4-amino-6-methyl-tetrazolo[1,5-b]pyridazine group |

TABLE-continued

| Compound | Z | A | X | B |
|---|---|---|---|---|
| 45 | NC— | —CH=CH— | —COOH | 4,5-diamino-pyridazinyl-tetrazole |
| 46 | H₂NCO— | —CH=CH— | —COOH | 4,5-diamino-pyridazinyl-tetrazole |
| 47 | NC— | —C≡C— | —COOH | pyridazinyl-tetrazole |
| 48 | NC— | —C≡C— | —COOH | 4-amino-pyridazinyl-tetrazole |
| 49 | H₂NCO— | —C≡C— | —COOH | pyridazinyl-tetrazole |
| 50 | H₂NCO— | —C≡C— | —COOH | 4-amino-pyridazinyl-tetrazole |
| 51 | HOOC— | —CH=CH— | —COOH | pyridazinyl-tetrazole |
| 52 | HOOC— | —CH=CH— | —COOH | 4-amino-pyridazinyl-tetrazole |

The compounds of the present invention are prepared by a process comprising:

(a) reacting a compound of formula (II)

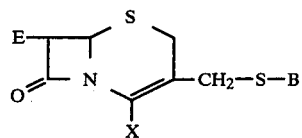

(II)

wherein
B and X are as defined above and E is amino or a group -N=C=Φ, wherein Φ is oxygen or sulphur, or a reactive derivative thereof, with an acid of formula (III)

Z—A—S—CH₂—COOH     (III)

wherein
Z and A are as defined above, or with a reactive derivative thereof; or (b) reacting a compound of formula (IV)

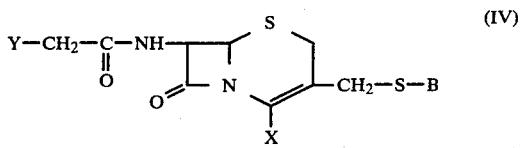

(IV)

wherein
B and X are as defined above and Y is halogen, or a salt thereof, with a compound of formula (V)

Z—A—SH     (V)

wherein Z and A are as defined above, or with a reactive derivative thereof;

(c) reacting a compound of formula (VI)

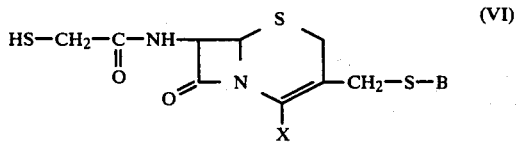

(VI)

wherein

B and X are as defined above, or a reactive derivative thereof, with a compound of formula (VIII)

Z—A—Y'    (VII)

wherein

Z and A are as defined above and Y' is halogen or the residue of an active ester of an alcohol; or (d) reacting a compound of formula (VIII)

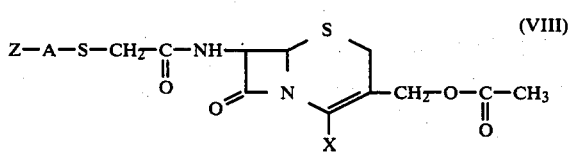

(VIII)

wherein

Z, A and X are as defined above, or a salt thereof, with a compound of formula (IX)

H—S—B    (IX)

wherein

B is as defined above, or a reactive derivative thereof; and, if desired, converting a compound of formula (I) into a pharmaceutically or veterinarily acceptable salt and/or, if desired, obtaining a free compound from a salt and/or, if desired, converting a compound of formula (I) or a salt thereof into another compound of formula (I) or a salt thereof and/or, if desired, resolving a mixture of isomers into the single isomers.

When in the compounds having the formulae (II), (IV), (VI) and (VIII) X is a free carboxy group, the carboxy group may be protected, if necessary, in a conventional manner before the reaction takes place.

Examples of protecting groups are those usually employed in the synthesis of peptides, for example, tert-butyl, benzhydryl, p-methoxybenzyl and p-nitrobenzyl. The protecting groups are then removed, at the end of the reaction, in a known manner, e.g., by mild acid hydrolysis.

The compounds of formula (I) containing the protecting groups are also included in the object of the present invention.

The starting materials used in each of the above mentioned processes (a) to (d), when one or more asymmetric carbon atoms are present, may be either optically active or racemic compounds.

Moreover, the starting materials, when, e.g., a group —CH=CH— is present, may be either the cis-isomers or the trans-isomers; when there are, e.g., two —CH=CH— groups, the starting materials may be either the cis,cis-isomers, or the trans,trans-isomers or the cis,-trans-isomers or the trans,cis-isomers.

A reactive derivative of the compound of formula (II) may be, for example, an amine salt, a silyl ester or a metal salt when X is carboxy.

A reactive derivative of the compound of formula (III) is, for example, an acyl halide, an anhydride or a mixed anhydride, an amide, an azide, a reactive ester or a salt, such as, for instance, the salts formed with alkaline or alkaline-earth metals, ammonia or an organic base.

A reactive derivative of the compounds of formulae (V), (VI) and (IX) is preferably a salt thereof, for example, an alkaline or alkaline-earth metal salt.

When Y or Y' are halogen, the halogen is preferably chlorine or bromine. When Y' is the residue of an active ester of an alcohol, it is preferably -O-mesyl or -O-tosyl.

The reaction between the compound of formula (II) or a reactive derivative thereof and the compound of formula (III) or a reactive derivative thereof may be performed either at room temperature or under cooling, in a suitable solvent, such as, e.g., acetone, dioxane, tetrahydrofuran, acetonitrile, chloroform, methylene chloride, dimethylformamide, 1,2-dichloro-ethane and, if desired, in the presence of a base such as, for example, sodium bicarbonate, potassium bicarbonate or a trialkylamine, or in the presence of another acid acceptor, such as an alkylene oxide, e.g., propylene oxide.

When the compound of formula (III) is reacted with the compound of formula (II) wherein E is amino, as a free acid or as a salt, it is desirable that the reaction be performed in the presence of a condensing agent, such as, for instance, N,N'-dicyclohexylcarbodiimide.

The reaction of the compound of formula (IV), or a salt thereof, with the compound of formula (V), or a reactive derivative thereof, for example a salt, is preferably carried out at temperatures ranging from about −30° C. to about +90° C., preferably at room temperature in the presence of an inorganic or organic base, such as, for instance, sodium or potassium hydroxides, sodium carbonate and triethylamine, in a suitable solvent which may be, for instance, acetone, chloroform, methanol, ethanol, methylene chloride and water. When in the compound of formula (V) the —SH group is not salified, it is preferable to carry out the reaction in the presence of a base, such as, for example, an alkaline carbonate, an alkaline hydroxide or triethylamine. The reaction between the compound of formula (VI), or a reactive derivative thereof, e.g., an alkaline salt, and the compound of formula (VII) may be performed either in an aqueous medium and in the presence of an inorganic base or in an organic solvent, preferably in an anhydrous organic solvent, such as, for example, methylene chloride, chloroform, dioxane, in the presence of an organic base; the reaction temperatures range from about −20° C. to about +50° C.

The reaction between the compound of formula (VIII), or a salt thereof, and the compound of formula (IX), or a reactive derivative thereof, for example, an alkaline salt, is preferably carried out in an inert organic solvent, such as, for instance, ethanol, dimethylformamide, dioxane, acetone, methylenechloride and chloroform; when a salt of the compound of formula (VIII) is used, e.g., when in the compound of formula (VIII) X is a salified carboxy group, then water or a solvent mixable with water or a mixture of water and organic solvents such as acetone, ethanol, dioxane and tetrahydrofuran are preferably employed. The reaction temperatures range from about 5° C. to about 90° C. and the pH from about 5 to about 7.5. If necessary, a buffer is used such as, for example, sodium phosphate or acetate. When in the compound of formula (VIII) X is a salified carboxy group, the salifying agent is preferably an alkaline or alkaline-earth hydroxide.

The optional salification of the compound of formula (I) as well as the optional conversion of a salt into a free compound, may be carried out according to conventional methods, i.e. methods already known in organic chemistry. As stated above, a compound of formula (I) or a salt thereof, may be converted into another compound of formula (I) or a salt thereof; also those optional conversions may be performed by conventional methods.

These optional conversions may be, e.g., the esterification of a compound of formula (I), wherein X is carboxy, which may be carried out by reacting the compound of formula (I), wherein the carboxy group is free or salified, for example in the form of a sodium, potassium, calcium or triethylammonium salt, with the suitable halide, in an organic solvent, such as acetone, tetrahydrofuran, chloroform, methylene chloride dimethylformamide, dimethylsulphoxide, or in a mixture of water and an organic solvent, e.g., dioxane and acetone; the reaction temperatures range from about $-20°$ C. to about $+80°$ C.

Furthermore a compound of formula (I), wherein X is an esterified carboxy group, may be saponified using, for example, an inorganic acid, such as hydrochloric acid or trifluoroacetic acid, as is known in organic chemistry.

Also the optional resolution of a mixture of isomers into the single isomers may be carried out by conventional methods. Thus, racemic compounds may be resolved into the optical antipodes, for example, by resolution, e.g., by means of fractionated crystallization of mixtures of diastereoisomeric salts, and, if desired, liberating the optical antipodes from the salts.

The compound of formula (II), wherein E is amino, may be prepared, for example, by reacting 7-aminocephalosporanic acid or a salt thereof with the compound of formula (IX), using reaction conditions well known in literature. The compound of formula (II), wherein E is -N=C=Φ may be prepared, e.g., by reacting a compound of formula (II), wherein E is amino, with phosgene or thiophosgene, in the presence of a hydrochloric acid acceptor, using known methods.

The compound of formula (III) may be prepared according to one of the following methods:

(1) by reaction of a compound of formula (VIIa)

    (VIIa)

wherein Z and A are as defined above and Y″ is halogen, preferably chlorine or bromine, or O-tosyl or O-mesyl, with a compound of formula (X)

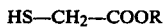    (X)

wherein R is hydrogen or $C_1$-$C_6$ alkyl, preferably ethyl or tert-butyl or diphenylmethyl; when R is $C_1$-$C_6$ alkyl the reaction product is saponified by known methods.

The reaction of the compound of formula (VIIa) with the compound of formula (X) is preferably performed in water or in an organic solvent, such as tetrahydrofuran, diethyl ether, benzene, or in a mixture of an organic solvent, e.g., one of those mentioned above, with water, in the presence of about 2-2.5 equivalents of a base when R is hydrogen and about 1-1.5 equivalents of basis when R is $C_1$-$C_6$ alkyl, and at temperatures ranging from about $-10°$ C. to about $+25°$ C. A suitable base is, for example, sodium hydroxide, sodium bicarbonate or triethylamine.

When in the compounds of formula (VIIa) A is, e.g., cis—CH=CH—, a compound of formula (III) is obtained wherein A is cis—CH=CH— and viceversa, when in the compounds of formula (VIIa) A is, e.g., trans—CH=CH—, a compound of formula (III) is obtained wherein A is trans—CH=CH—;

(2) by reaction of a compound of formula (X) with a compound of formula (XI)

    (XI)

so obtaining a compound of formula (III), wherein A is —CH=CH— (cis or trans). When the reaction between the compound of formula (X) and the compound of formula (XI) is performed in a protic solvent, preferably in an aqueous protic solvent, e.g. water or lower aliphatic alcohols, e.g. ethanol in the presence of not more than an equivalent of a base, e.g. triethylamine, an alkaline bicarbonate, an alkaline hydroxide, and at low temperatures preferably about 0° C., a compound of formula (III) is obtained wherein A is cis—CH=CH—.

When the same reaction is carried out in the same solvents and in the presence of the same bases but at temperatures higher than the room temperature, or in an excess of the thiolate anion or with the use of acid catalyst, e.g., HCl, a compound of formula (III) is obtained wherein A is a mixture of cis—CH=CH— and trans—CH=CH—. The separation of the obtained isomers may be carried out by the usual methods employed in organic chemistry for the separation of geometric isomers such as, for example, fractional crystallization from solvents such as, for instance, water or lower aliphatic alcohols, e.g. ethanol, or by chromatographic separation.

Futhermore, a compound of formula (III) wherein Z is cyano may be obtained from the compound of formula (III) wherein Z is carbamoyl either by treatment with a dehydrating agent, such as phosphorus pentachloride, phosphorus oxychloride or triphenylphosphine in an organic solvent such as a mixture of dimethylformamide and ethyl ether, carbonium tetrachloride, triethylamine and N,N'-dicyclohexylcarbodiimmide at room temperature or by heating to about 30°-120° C. in an organic solvent preferably selected from the group consisting of hexamethylphosphoric triamide and dimethyl sulphoxide. The compound of formula (IV) may be prepared by reacting the compound of formula (II) with a compound of formula (XII)

    (XII)

wherein Y is as defined above, or with a halide or a reactive thereof. The reaction between the compound of formula (II) and the compound of formula (XII), or a halide or a reactive derivative thereof, is preferably carried out in an aqueous or anhydrous organic solvent such as, e.g., acetone, dioxane, tetrahydrofuran, acetonitrile, chloroform, methylene chloride, dimethylformamide, in the presence of an organic or inorganic base, such as sodium hydroxide or triethylamine, at temperatures ranging from about $-10°$ C. to about $+25°$ C. For instance, acid halides, anhydrides or mixed anhydrides, azides, amides, reactive esters and salts may be used as reactive derivatives of the compound of formula (XII).

The compound of formula (VI) may be prepared, for example, by reacting the compound of formula (II) with a compound of formula (X) wherein R is hydrogen and using reaction conditions analogous to those employed for the reaction between the compound of formula (II) and the compound of formula (III).

The compound of formula (VIII) may be prepared, for example, by reacting 7-amino-cephalosporanic acid or a salt thereof with a compound of formula (III), using reaction conditions analogous to those employed for the reaction between the compound of formula (II) and the compound of formula (III).

The compounds of formulae (V), (VII), (VIIa), (IX) as well as the compounds of formulae (X), (XI) and (XII) may be easily prepared by known methods starting from known compounds or, respectively, they are compounds already known in literature.

The compounds object of the present invention own a high antibacterial activity either in animals or in humans against both Gram-positive and Gram-negative bacteria and are therefore useful in the treatment of the infections caused by said microorganisms, such as, respiratory tract infections, for example, bronchitis, bronchopneumonia, pleurisy; hepatobiliary and abdominal infections, for example, cholecystitis, peritonitis; blood and cardiovascular infections, for example, septicemia; urinary tract infections, for example, pyelonephritis, cystitis; obstetrical and gynecological infections, for instance, cervicitis, endometritis; ear, nose and throat infections, for instance, otitis, sinusitis, parotitis.

The following Table shows the minimal inhibiting concentrations (MIC) in μg/ml of the compounds of the invention identified by the codes K 13040, K 13102, K 13113, K 13126, K 13141 and K 13156, against both Gram-positive bacteria and Gram-negative bacteria in comparison with the known compounds K 9227 and K 10299 (which are the most active compounds among those of the British Patent Specification No. 1.478.055, corresponding to U.S. patent application Ser. No. 485,276 of July 2, 1974), Cefazolin and Cefamandole.

positive bacteria but they own also a very high activity against Gram-negative bacteria: they are therefore much more useful than the known compounds of the Table, for the treatment of infections caused by Gram-negative bacteria such as, for example, urinary tract infections and respiratory tract infections.

In particular, the Table shows that the compound K 13102 is about 8 times more active than Cefazolin against staphylococci, about 8 times more active than Cefazolin against streptococci (including diplococci) and about 6 times more active than Cefazolin against Gram-negative bacteria. Furthermore the compound K 13102 was tested on a series of 60 strains of Gram-negative microorganisms comprising Klebsiella, *Escherichia coli*, and Proteus mirabilis in comparison with Cefazolin and the compound K 13102 was always found to be more active than Cefazolin.

Against the Haemophylus influenzae (Gram-negative bacterium: 7 strains tested), the compound K 13102 was about 14 times more active than Cefazolin and 2 times more active than Cefamandole.

Besides, the Table shows that the compound K 13040 is about 3 times more active then Cefazolin against staphylococci, about 5 times more active than Cefazolin against streptococci (including diplococci) and about 2 times more active than Cefazolin against Gram-negative bacteria. Against the Haemophylus influenzae (7 strains tested) the compound K 13040 was about 8 times more active than Cefazolin. Moreover, on the average the compound K 13156 is about 8 times more active than Cefazolin against Gram-negative bacteria.

Furthermore, the compounds K 13040, K 13102, K 13113, K 13126, K 13141 and K 13156 are more active than the reference compounds reported in the preceding Table also in the in vivo tests, e.g., in the experimental infection induced on mouse by *Staphylococcus aureus* Smith, *Escherichia coli* G and Klebsiella pneumoniae ATCC 10031. For example, the compounds K 13040 and K 13156 are about 4 times more active than Cefazolin in vivo in the experimental infection induced on mouse by *Escherichia coli* G.

TABLE

| | (MIC μg/ml) | | | | | | | | | |
|---|---|---|---|---|---|---|---|---|---|---|
| | Cefazolin | Cefamandole | K 9227 | K 10299 | K 13040 | K 13102 | K 13113 | K 13126 | K 13141 | K 13156 |
| Gram-positive bacteria: | | | | | | | | | | |
| Staphylococcus aureus Smith | 0.05 | 0.15 | 0.05 | 0.075 | 0.018 | 0.006 | 0.012 | 0.03 | 0.025 | 0.05 |
| Diplococcus aureus 39/2 | 0.6 | 1.2 | 0.2 | 0.4 | 0.1 | 0.05 | 0.1 | 0.28 | 0.14 | 0.5 |
| Diplococcus pneumoniae ATCC6301 | 0.05 | 0.019 | 0.4 | 0.2 | ≦0.006 | ≦0.006 | ≦0.006 | ≦0.006 | 0.012 | 0.02 |
| Streptococcus β-haemolyticus C203 | 0.05 | 0.019 | 0.025 | 0.037 | ≦0.006 | ≦0.006 | ≦0.006 | ≦0.006 | 0.012 | 0.02 |
| Gram-negative bacteria: | | | | | | | | | | |
| Escherichia coli G | 1.6 | 2.35 | 3.1 | 0.8 | 0.8 | 0.4 | 0.8 | 0.8 | 0.6 | 0.8 |
| Escherichia coli 1507 | 1.6 | 0.8 | 1.6 | 0.8 | 0.4 | 0.2 | 0.4 | 0.8 | 0.6 | 0.8 |
| Klebsiella pneumoniae ATCC10031 | 0.8 | 0.15 | 0.4 | 0.2 | 0.2 | 0.05 | 0.2 | 0.2 | 0.2 | 0.2 |
| Klebsiella aerogenes 1522E | 1.1 | 0.4 | 1.6 | 0.8 | 0.3 | 0.2 | 0.2 | 0.6 | 0.28 | 0.1 |
| Enterobacter aerogenes ATCC8308 | 1.2 | 1.6 | 1.2 | 0.6 | 0.6 | 0.4 | 0.6 | 0.8 | 0.4 | 0.2 |
| Enterobacter cloacae 1321E | 3.1 | 1.6 | 3.1 | 1.6 | 1.2 | 1.6 | 1.6 | 0.56 | 0.8 | 0.1 |
| Salmonella typhi Watson | 1.6 | 0.6 | 0.8 | 0.2 | 0.4 | 0.2 | 0.2 | 0.07 | 0.2 | 0.1 |
| Shigella sonnei ATCC11060 | 1.6 | 2.35 | 1.6 | 1.6 | 1.6 | 1.6 | 0.8 | 0.8 | 1.6 | 1.6 |
| Proteus mirabilis ATCC9921 | 6.2 | 1.6 | 12.5 | 6.2 | 0.8 | 0.4 | 0.8 | 0.8 | 1.6 | 0.05 |

Cefazolin = 7-(1-(1H)—tetrazolylacetamido)-3-[2-(5-methyl-1,3,4-thiadiazolyl)-thiomethyl]-3-cephem-4-carboxylic acid;
Cefamandole = 7-D-mandelamido-3-{[(1-methyl-1H—tetrazol-5-yl)-thio]-methyl}-3-cephem-4-carboxylic acid;
K 9227 = 7-[(cyanomethyl-thio)-acetamido]-3-[2-(5-methyl-1,3,4-thiadiazolyl)-thiomethyl]-3-cephem-4-carboxylic acid;
K 10299 = 7-[(cyanomethyl-thio)-acetamido]-3-[5-(1-methyl-1,2,3,4-tetrazolyl)-thiomethyl]-3-cephem-4-carboxylic acid;
K 13040 = 7-[β-carboxamido-ethylene(cis)-thio-acetamido]-3-[(tetrazolo[1,5-b]pyridazin-8-amino-6-yl)-thiomethyl]-3-cephem-4-carboxylic acid;
K 13102 = 7-[β-cyano-ethylene(cis)-thio-acetamido]-3-[(tetrazolo[1,5-b]pyridazin-8-amino-6-yl)-thiomethyl]-3-cephem-4-carboxylic acid;
K 13113 = 7-[β-cyano-ethylene(cis)-thio-acetamido]-3-[(tetrazolo[1,5-b]pyridazin-6-yl)-thiomethyl]-3-cephem-4-carboxylic acid;
K 13126 = 7-[β-carboxamido-ethylene(cis)-thio-acetamido]-3-[(1-ethyl-1,2,3,4-tetrazol-5-yl)-thiomethyl]-3-cephem-4-carboxylic acid;
K 13141 = 7-[β-cyano-ethylene(cis)-thio-acetamido]-3-[(5-amino-1,3,4-thiadiazol-2-yl)-thiomethyl]-3-cephem-4-carboxylic acid;
K 13156 = 7-[β-cyano-ethylene(cis)-thio-acetamido]-3-[(1-β-carboxyethyl-1,2,3,4-tetrazol-5-yl)-thiomethyl]-3-cephem-4-carboxylic acid.

As is evident from the Table, the compounds of the invention show not only a high activity against Gram- The compounds of the invention may be administered, either to humans or to animals, in a variety of dosage forms, e.g., orally in the form of tablets, capsules, drops or syrups; rectally in the form of suppositories; parenterally, e.g., intravenously or intramuscolarly (as solutions or suspensions), with intravenous administration being preferred in emergency situation; by inhalation in the form of aerosols or solutions for nebulizers; intravaginally in the form, e.g. of bougies; or topically in the form of lotions, creams and ointments. The pharmaceutical or veterinary compositions containing the compounds of the invention may be prepared in a conventional way by employing the conventional carriers and/or diluents used for the other cephalosporins. Conventional carriers or diluents are, for example water, gelatine, lactose, starches, magnesium stearate, talc, vegetable oils, cellulose and the like. Daily doses in the range of about 1 to about 100 mg per kg of body weight may be used, in various animal species, the exact dose depending on the age, weight and condition of the subject to be treated and on the frequency and route of administration. A preferred way of administration of the compounds of the invention is the parenteral one: in this case the compounds may be administered, for example to adult humans, in an amount ranging from about 100 mg to about 200 mg pro dose, preferably about 150 mg pro dose, 1-4 times a day, dissolved in a suitable solvent, such as, for example sterile water or lidocaine hydrochloride solution for intramuscolar injections, and sterile water, physiological saline solution, dextrose solution or the conventional intravenous fluids or electrolytes, for intravenous injections.

Futhermore, the compounds of the invention may be used as antibacterial agents in a prophylactic manner, e.g., in cleaning or as surface disinfecting compositions, for example, at a concentration of about 0.2 to 1% by weight of such compounds admixed with, suspended or dissolved in conventional inert dry or aqueous carriers for application by washing or spraying.

They are also useful as nutritional supplements in animal feeds.

Assessment of melting points was somewhat difficult in some cases, as the compounds tend to retain the solvent. In these cases, after the indication of the melting point, the word "dec." (decomposition) was added.

The I.R. spectra were determined in a solid phase on a Perkin-Elmer 125 spectrophotometer, while the U.V. spectra were usually evaluated in a buffer phosphate solution at pH 7.4 on a Bausch-Lomb apparatus. N.M.R. spectra were determined in DMSO (dimethylsulphoxide) with a Varian HA-100 spectrometer with $(CH_3)_4Si$ as internal standard. The following examples illustrate but do not limit the present invention.

EXAMPLE 1

To a solution of $\beta$-cyano-ethylene(cis)-thio-acetic acid (1.44 g) and triethylamine (1.4 ml) in anhydrous acetone (80 ml), some drops of N-methylmorpholine were added. The solution was cooled at 0° C. and then pivaloylchloride (1.22 ml) dissolved in anhydrous acetone (20 ml) was added under stirring. The mixture was stirred at 0° C. for 30 minutes, then a solution containing 7-amino-3-[(1-ethyl-1,2,3,4-tetrazol-5-yl)-thiomethyl]-3-cephem-4-carboxylic acid (3.42 g) and triethylamine (1.4 ml) in 50% acetone (160 ml) was added. After the addition the solution was stirred for 1 hour at 0° C. and afterwards for 2 hours at room temperature. The acetone was evaporated under vacuum. The residue was taken up with water and washed with ethyl acetate. After separation, the aqueous phase was stratified with ethyl acetate and brought to pH=2 with 20% $H_2SO_4$. The residue was filtered off and the organic phase was separated, dried on anhydrous $Na_2SO_4$ and evaporated to small volume; the residue was taken up with ethyl ether so obtaining 7-[$\beta$-cyano-ethylene(cis)-thio-acetamido]-3-[(1-ethyl-1,2,3,4-tetrazol-5-yl)-thiomethyl]-3-cephem-4-carboxylic acid (2.8 g; yield 60%), m.p. 80°-83° C. (dec.);

Analysis: Found: C 41.32; H 3.83; N 20.40; S 20.28; $C_{16}H_{17}N_7O_4S_3$ requires C 41.10; H 3.67; N 20.97; S 20.57;

U.V. (pH 7.4 buffer phosphate): $\lambda_{max}=272$ m$\mu$; $E_{1cm}^{1\%}=416$;

T.L.C.: $R_f=0.51$ ($CHCl_3:CH_3OH:HCOOH=160:40:20$);

I.R. (KBr): $\nu(C\equiv N)$ conjugated 2210 cm$^{-1}$; $\nu(C=O)$ $\beta$-lactam 1775 cm$^{-1}$; $\nu(C=O)$ amide 1680 cm$^{-1}$. $\nu(C-N)+\delta(N-H)$ sec. amide 1540 cm$^{-1}$;

N.M.R. ppm (DMSO-d$_6$); ;b 3.68 (2H, q, 2-CH$_2$); 3.73 (2H, s, —S—CH$_2$—CO); 4.31 (2H, q, 3-CH$_2$); 5.10 (1H, d, 6—H); 5.63 (1H, d-d, 7-11); 5.72 (1H, d, NC—CH=); 7.63 (1H, d, =CH—S); $J_{CH=CH(cis)}=11$ Hz; 9.2 (1H, d, —CONH).

By proceeding analogously, the following compounds were obtained:

7-[$\beta$-cyano-ethylene(cis)-thio-acetamido]-3-[(1-(2)-propenyl-1,2,3,4-tetrazol-5-yl)-thiomethyl]-3-cephem-4-carboxylic acid;

7-[$\beta$-cyano-ethylene(cis)-thio-acetamido]-3-[(1-(1)-propenyl-1,2,3,4-tetrazol-5-yl)-thiomethyl]-3-cephem-4-carboxylic acid.

$\beta$-cyano-ethylene(cis)-thio-acetic acid used as starting material was prepared as follows:

To a solution of $\beta$-carboxamido-ethylene(cis)-thio-acetic acid (4 g) in dimethylformamide/ethyl ether (3:2; 100 ml), cooled at 0° C., phosphorus pentachloride (5.2 g) was added under stirring, maintaining the temperature between 8° and 10° C. The solution was then stirred for 2 hours between 0° and 10° C.

The solution was poured into ice and the ethereal layer was separated; the aqueous layer was extracted four times with ethyl acetate (4×50 ml). The combined extracts were dried on $Na_2SO_4$ and then evaporated to dryness at a temperature not higher than 40° C., so obtaining a yellowish oil which was dissolved in methanol (10 ml). To the resulting solution the stoichiometric amount of dicyclohexylamine was added, so obtaining the precipitation of the dicyclohexylamine salt of $\beta$-cyano-ethylene(cis)-thio-acetic acid which, after filtration, was repeatedly washed with ethyl ether (m.p. 180°-183° C.). The salt was dissolved in water/ethyl acetate (5:7; 120 ml) at 5° C.; the solution was acidified by dropwise addition of 40% $H_3PO_4$ (10 ml). The resulting solution was extracted three times with ethyl acetate and the combined organic extracts were washed with water, saturated with NaCl, dried on $Na_2SO_4$ and evaporated to dryness under vacuum to obtain $\beta$-cyano-ethylene(cis)-thio-acetic acid (2.76 g; yield 77%; m.p. 90°-92° C).

Analysis: Found: C 41.70; H 3.63; N 9.64; S 22.25; $C_5H_5NO_2S$ requires: C 41.94; H 3.52; N 9.78; S 22.39.

I.R. (KBr): $\nu(C\equiv N)$ conjugated 2220 cm$^{-1}$ $\nu(C=O)$ acid 1720 cm$^{-1}$ N.M.R. (DMSO-d$_6$): 5.4 $\delta$(d, NC-CH=), 7.4 $\delta$(d, =CH-S) $J_{CH=CH(cis)}=10$ Hz.

EXAMPLE 2

To a solution containing β-cyano-ethylene(cis)-thio-acetic acid (2.88 g) and triethylamine (2.8 g) in anhydrous acetone (160 ml) some drops of N-methylmorpholine were added. The mixture was cooled at −10° C. and then pivaloylchloride (2.44 ml) dissolved in anhydrous acetone (40 ml) was added under stirring and then, after stirring for 30 minutes at −10° C., a solution containing 7-amino-3-[(1-β-carboxyethyl-1,2,3,4-tetrazol-5-yl)-thiomethyl]-3-cephem-4-carboxylic acid (7.72 g) and triethylamine (5.6 ml) in 50% acetone (320 ml), cooled at 0° C., was added after 30 minutes.

The mixture was then stirred at 0° C. for 1 hour and afterwards at room temperature for 3 hours. The acetone was evaporated under vacuum. The residue was taken up with water, stratified with ethyl acetate and the pH of the mixture was brought to 2.5 with 40% $H_3PO_4$. After filtration, the ethyl acetate was separated and the organic phase was washed with water, dried on $Na_2SO_4$ and evaporated to small volume. Ethyl ether was added to give a solid, which was filtered and stirred with ethyl ether. The solid was filtered again so obtaining 5.1 g (yield 50%) of 7-[β-cyano-ethylene(cis)-thio-acetamido]-3-[(1-β-carboxyethyl-1,2,3,4-tetrazol-5-yl)-thiomethyl]-3-cephem-4-carboxylic acid, m.p. 118°–120° C. (dec.).

Analysis: Found: C 40.10; H 3.42; N 19.11; S 18.10; $C_{17}H_{17}N_7O_6S_3$ requires: C 39.91; H 3.35; N 19.17; S 18.80.

U.V. (pH 7.4 buffer phosphate): $\lambda_{max}$=273 mμ $E_1$ $_{cm}1\%$=416

T.L.C.: $R_f$=0.49 ($CHCl_3$:$CH_3OH$:H-COOH=160:40:20)

I.R. (KBr): $\nu(C\equiv N)$ conjugated 2200 $cm^{-1}$; $\nu(C=O)$ β-lactam 1780 $cm^{-1}$; $\nu(C=O)$ acid 1720 $cm^{-1}$; $\nu(C-N)+\nu(N-H)$ sec. amide 1540 $cm^{-1}$;

N.M.R. ppm (DMSO-$d_6$) 2.93 (2H, t, —CH$_2$—COOH on tetrazole ring); 3.83 (4H, br-s, —S—CH$_2$—CO— and 2—CH$_2$); 4.4 (4H, m, >N—CH$_2$— and 3—CH$_2$—); 5.08 (1H, d, 6-H); 5.69 (1H, d-d, 7-H); 5.72 (1H, d, NC-CH=); 7.66 (1H, d, =CH-S) $J_{CH=CH(cis)}$=11 Hz; 9.2 (1H, d, —CONH).

EXAMPLE 3

By using the same method of example 2 and reacting β-cyano-ethylene(cis)-thio-acetic acid with 7-amino-3-[(1-carboxy-methyl-1,2,3,4-tetrazol-5-yl)-thiomethyl]-3-cephem-4-carboxylic acid, 7-[β-cyano-ethylene(cis)-thio-acetamido]-3-[(1-carboxymethyl-1,2,3,4-tetrazol-5-yl)-thiomethyl]-3-cephem-4-carboxylic acid (yield 52%) was obtained.

Analysis: Found: C 38.41; H 3.11; N 19.50; S 19.10; $C_{16}H_{15}N_7O_6S_3$ requires: C 38.62; H 3.04; N 19.71; S 19.33.

U.V. (pH 7.4) buffer phosphate): $\lambda_{max}$=273 mμ $E_1$ $_{cm}1\%$=420

T.L.C.: $R_f$=0.59 ($CHCl_3$:$CH_3OH$:H-COOH=160:40:20)

I.R. (KBr) $\nu(C\equiv N)$ conjugated 2200 $cm^{-1}$; $\nu(C=O)$ β-lactam 1780 $cm^{-1}$; $\nu(C=O)$ acid 1720 $cm^{-1}$; $\nu(C-N)+\delta(N-H)$ sec. amide 1540 $cm^{-1}$.

N.M.R.: ppm (DMSO-$d_6$); 3.83 (4H, br-s, —S—CH$_2$—CO— and 2—CH$_2$); 4.1 (2H, s, >N—CH$_2$—COOH); 4.4 (2H, q, 3—CH$_2$); 5.08 (1H, d, 6—H); 5.68 (1H, d-d, 7—H); 5.72 (1H, d, NC—CH=); 7.66 (1H, d, =CH—S) $J_{CH=CH(cis)}$=11 Hz; 9.2 (1H, d, CO—NH).

Analogously, the following compounds were prepared:

7-[β-cyano-ethylene(cis)-thio-acetamido]-3-[(1-γ-carboxypropyl-1,2,3,4-tetrazol-5-yl)-thiomethyl]-3-cephem-4-carboxylic acid;

7-[β-cyano-ethylene(cis)-thio-acetamido]-3-[(1-β-carboxyethylene-1,2,3,4-tetrazol-5-yl)-thiomethyl]-3-cephem-4-carboxylic acid;

7-[β-cyano-ethylene(cis)-thio-acetamido]-3-[(1-carboxy-methyl-oxy-iminomethyl-1,2,3,4-tetrazol-5-yl)-thiomethyl]-3-cephem-4-carboxylic acid;

7-[β-cyano-ethylene(cis)-thio-acetamido]-3-[(1-carboxamido-methyl-1,2,3,4-tetrazol-5-yl)-thiomethyl]-3-cephem-4-carboxylic acid;

7-[β-cyano-ethylene(cis)-thio-acetamido]-3-[(1-β-carboxamidoethyl-1,2,3,4-tetrazol-5-yl)-thiomethyl]-3-cephem-4-carboxylic acid;

7-[β-cyano-ethylene(cis)-thio-acetamido]-3-[(1-sulfomethyl-1,2,3,4-tetrazol-5-yl)-thiomethyl]-3-cefem-4-carboxylic acid;

7-[β-cyano-ethylene(cis)-thio-acetamido]-3-[(1-β-sulfoethyl-1,2,3,4-tetrazol-5-yl)-thiomethyl]-3-cephem-4-carboxylic acid;

7-[β-cyano-ethylene(cis)-thio-acetamido]-3-[(1-β-sulfoethylene-1,2,3,4-tetrazol-5-yl)-thiomethyl]-3-cephem-4-carboxylic acid;

7-[β-cyano-ethylene(cis)-thio-acetamido]-3-[(1-β-dimethylaminoethyl-tetrazol-5-yl)-thiomethyl]-3-cephem-4-carboxylic acid;

7-[β-cyano-ethylene(cis)-thio-acetamido]-3-[(5-carboxymethyl-amino-1,3,4-thiadiazol-2-yl)-thiomethyl]-3-cephem-4-carboxylic acid;

7-[β-cyano-ethylene(cis)-thio-acetamido]-3-[(5-carboxymethyl-1,3,4-thiadiazol-2-yl)-thiomethyl]-3-cephem-4-carboxylic acid;

7-[β-cyano-ethylene(cis)-thio-acetamido]-3-[(5-succinamido-1,3,4-thiadiazol-2-yl)-thiomethyl]-3-cephem-4-carboxylic acid;

7-[β-cyano-ethylene(cis)-thio-acetamido]-3-[(5-maleamido-1,3,4-thiadiazol-2-yl)-thiomethyl]-3-cephem-4-carboxylic acid;

7-[β-cyano-ethylene(cis)-thio-acetamido]-3-[(5-β-carboxyethylene-1,3,4-thiadiazol-2-yl)-thiomethyl]-3-cephem-4-carboxylic acid;

7-[β-cyano-ethylene(cis)-thio-acetamido]-3-[(5-β-carboxyethyl-1,3,4-thiadiazol-2-yl)-thiomethyl]-3-cephem-4-carboxylic acid;

7-[β-cyano-ethylene(cis)-thio-acetamido]-3-[(5-ureido-1,3,4-thiadiazol-2-yl)-thiomethyl]-3-cephem-4-carboxylic acid.

EXAMPLE 4

To a solution containing β-cyano-ethylene(cis)-thio-acetic acid (2.88 g) and triethylamine (2.8 ml) in anhydrous acetone (120 ml), some drops of N-methylmorpholine were added; the solution was cooled at −10° C. and then pivaloylchloride (2.44 ml) dissolved in anhydrous acetone (30 ml) was added under stirring. The mixture was stirred for 30 minutes at −10° C., then a solution containing 7-amino-3-[(5-amino-1,3,4-thiadiazol-2-yl)-thiomethyl]-3-cephem-4-carboxylic acid (6.80 g) and triethylamine (2.8 ml) in 50% acetone (240 ml), was added, the mixture was cooled at −20° C. for 30 minutes, then stirred at −20° C. for 1 hour and at room temperature for 2 hours. The acetone was evaporated under vacuum, the residue was diluted with water, stratified with ethyl acetate and brought to pH 2.5 with 40% $H_3PO_4$. The residue was filtered off and the ethyl acetate separated; the organic phase was washed with water, dried on $Na_2SO_4$ and evaporated to small volume. By adding ethyl ether, a solid was obtained which was filtered and then stirred with ethyl ether so obtaining, after filtration, 7-[β-cyano-ethylene(cis)-thio-acetamido]-3-[(5-amino-1,3,4-thiadiazol-2-yl)-thiomethyl]-3-cephem-4-carboxylic acid, (5.64 g-60%), m.p. 135°-138° C. (dec.).

Analysis: Found: C 38.37; H 3.25; N 17.48; S 26.81; $C_{15}H_{14}N_6O_4S_4$ requires: C 38.28; H 3.00; N 17.86; S 27.26.

U.V. (pH 7.4 buffer phosphate): $\lambda_{max}=273$ mμ $E_1$ $cm^{1\%}=434$

T.L.C.: $R_f=0.32$ (CHCl$_3$:CH$_3$OH:H-COOH=160:40:20);

I.R. (KBr): ν(C≡N) conjugated 2225 cm$^{-1}$; ν(C=O) β-lactam 1770 cm$^{-1}$; ν(C=O) acid 1670 cm$^{-1}$; ν(C-N)+δ(N-H) sec. amide 1550 cm$^{-1}$.

EXAMPLE 5

To a solution containing β-cyano-ethylene(cis)-thio-acetic acid (0.72 g) and triethylamine (0.70 ml) in anhydrous acetone (40 ml) two drops of N-methyl-morpholine were added. The solution was cooled between 0° C. and +5° C. and then pivaloylchloride (0.61 ml) dissolved in anhydrous acetone (10 ml) was added under stirring. The mixture was stirred for 30 minutes at the same temperature, then a solution of 7-amino-3-[(tetrazolo[1,5-b]pyridazin-8-amino-6-yl)-thiomethyl]-3-cephem-4-carboxylic acid (1.90 g) and triethylamine (0.7 ml) in 50% aqueous acetone (80 ml) was added, maintaining the temperature at about 0° C. The solution was stirred at 0°-5° C. for 1 hour then at room temperature for 2 hours. The acetone was evaporated under vacuum, the residue was diluted with water, stratified with ethyl acetate and brought to a pH of about 2 with 20% $H_2SO_4$. The residue was filtered off, the ethyl acetate was separated; the organic phase was washed with water, dried on $Na_2SO_4$ and evaporated to dryness, so obtaining a raw product which after purification by grinding with a little of ethyl acetate gave 7-[β-cyano-ethylene(cis)-thio-acetamido]-3-[(5-tetrazolo[1,5-b]pyridazin-8-amino-6-yl)-thiomethyl]-3-cephem-4-carboxylic acid (1.25 g; 50%), m.p. 170°-175° C. (dec.).

Analysis: Found: C 39.80; H 3.06; N 24.60; S 18.40; $C_{17}H_{15}N_9O_4S_3$ requires: C 40.38; H 2.92; N 25.00; S 19.00.

U.V. (pH 7.4 buffer phosphate): $\lambda_{max}=272$ mμ $E_1$ $cm^{1\%}=640$

T.L.C.: $R_f=0.56$ (CHCl$_3$:CH$_3$OH:H-COOH=160:40:20)

I.R. (KBr): ν(C≡N) conjugated 2210 cm$^{-1}$; ν(C=O) β-lactam 1770 cm$^{-1}$; ν(N-H) 3300, 3150 cm$^{-1}$; ν(N-H) —NH$_2$ group 1630 cm$^{-1}$.

N.M.R. ppm (DMSO-d$_6$); 3.68 (2H, q, 2—CH$_2$); 3.73 (2H, s, —S—CH$_2$—CO); 4.31 (2H, q, 3—CH$_2$); 5.10 (1H, d, 6—H); 5.63 (1H, d-d, 7—H); 5.72 (1H, d, NC—CH=); 6.39 (1H, d, 7-H on the pyridazine ring); 7.67 (1H, d, =CH—S) $J_{CH=CH(cis)}=11$ Hz; 7.98 (2H, br-s, 8—NH$_2$ on the pyridazine ring); 9.2 (1H, d, —CONH).

EXAMPLE 6

By using the same method of example 5 the following compounds were prepared:

7-[β-cyano-ethylene(cis)-thio-acetamido]-3-[(tetrazolo[1,5-b]pyridazin-6-yl)-thiomethyl]-3-cephem-4-carboxylic acid;

Analysis: Found: C 41.49; H 3.11; N 22.51; S 19.22; $C_{17}H_{14}N_8O_4S_3$: requires C 11.62; H 2.87; N 22.84; S 19.61.

U.V. (pH 7.4 buffer phosphate): $\lambda_{max}=271$ mμ $E_1$ $cm^{1\%}=468$; $\lambda_{max}=242$ $E_1$ $cm^{1\%}=450$.

T.L.C. = $R_f=0.65$ (CHCl$_3$:CH$_3$OH:H-COOH=160:40:20)

I.R. (KBr) ν(C≡N) conjugated 2220 cm$^{-1}$; ν(C=O) β-lactam 1770 cm$^{-1}$; ν(C-N)+δ(N-H) sec. amide 1540 cm$^{-1}$ N.M.R. ppm (DMSO-d$_6$): 3.6 (1H, d, 2—CH$_2$); 3.71 (2H, s, —S—CH$_2$—CO); 3.85 (1H, d, 2—CH$_2$); 4.19 (1H, d, 3—CH$_2$); 4.6 (1H, d, 3—CH$_2$); 5.1 (1H, d, 6—H); 5.67 (1H, d-d, 7—H) J 6H-7H=5 Hz; 5.71 (1H, d, NC—CH=); 7.63 (1H, d, =CH—S) J CH=CH(cis)=10.5 Hz; 7.75 (1H, d, 8-H in the ring of pyridazine); 8.57 (1H, d, 7-H in the ring of pyridazine) J 7H-8H=9 Hz; 9.19 (1H, d, —CONH) J 7H-NH=8 Hz.

7-[β-cyano-ethylene(cis)-thio-acetamido]-3-{[tetrazolo[1,5-b]pyridazin-8-N(carboxymethyl)-6-yl]-thiomethyl}-3-cephem-4-carboxylic acid;

Analysis: Found: C 40.10; H 3.25; N 21.91; S 16.73; $C_{19}H_{17}N_9O_6S_3$ requires: C 40.48; H 3.04; N 22.36; S 17.06;

U.V. (pH 7.4 buffer phosphate): $\lambda_{max}=272$ mμ $E_1$ $cm^{1\%}=553$

T.L.C. = $R_f=0.39$ (CHCl$_3$:CH$_3$OH:H-COOH=160:40:20)

I.R. (KBr): ν(C≡N) conjugated 2200 cm$^{-1}$; ν(C=O) β-lactam 1760 cm$^{-1}$; ν(C=O) acid 1650 cm$^{-1}$; ν(C-N)+δ(N-H) sec. amide 1580 cm$^{-1}$.

7-[β-cyano-ethylene(cis)-thio-acetamido]-3-[(tetrazolo[1,5-b]pyridazin-8-carboxy-6-yl)-thiomethyl]-3-cephem-4-carboxylic acid:

Analysis: Found: C 40.11; H 2.91; N 2.61; S 17.36; $C_{18}H_{14}N_8O_6S_3$ requires: C 40.44; H 2.63; N 20.96; S 17.99.

U.V. (pH 7.4 buffer phosphate): $\lambda_{max}=270$ mμ $E_1$ $cm^{1\%}=490$

T.L.C.: $R_f=0.38$ (CHCl$_3$:CH$_3$OH:H-COOH=160:70:30)

I.R. (KBr): ν(C≡N) conjugated 2220 cm$^{-1}$; ν(C=O) β-lactam 1765 cm$^{-1}$; ν(C-N)+δ(NH) sec. amide 1530 cm$^{-1}$.

7-[β-cyano-ethylene(cis)-thio-acetamido]-3-[(tetrazolo[1,5-b]pyridazin-7-amino-8-yl)-thiomethyl]-3-cephem-4-carboxylic acid;

Analysis: Found: C 39.69; H 3.08; N 24.41; S 17.90; $C_{17}H_{15}N_9O_4S_3$ requires: C 40.38; H 2.92; N 25.00; S 19.00.

U.V. (pH 7.4 buffer phosphate): $\lambda_{max}=270$ mμ; $E_1$ $cm^{1\%}=464$; shoulder at 350 mμ $E_1$ $cm^{1\%}=100$ T.L.C.: $R_f=0.36$ (CHCl$_3$:CH$_3$OH:H-COOH=160:40:20)

I.R. (KBr): ν(C≡N) conjugated 2200 cm$^{-1}$; ν(C=O) β-lactam 1760 cm$^{-1}$; ν(C=O) acid 1560 cm$^{-1}$; ν(C-N)+δ(N-H) sec. amide 1530 cm$^{-1}$.

7-[β-cyano-ethylene(cis)-thio-acetamido]-3-[(tetrazolo[1,5-b]pyridazin-8-hydroxy-6-yl)-thiomethyl]-3-cephem-4-carboxylic acid;

7-[β-cyano-ethylene(cis)-thio-acetamido]-3-[(1,2,5-thiadiazolo[3,4-d]pyridazin-4-yl)-thiomethyl]-3-cephem-4-carboxylic acid;

7-[β-cyano-ethylene(cis)-thio-acetamido]-3-[(tetrazolo[4,5-a]pyrazin-6-yl)-thiomethyl]-3-cephem-4-carboxylic acid;

7-[β-cyano-ethylene(cis)-thio-acetamido]-3-[(tetrazolo[4,5-a]pyrazin-8-amino-6-yl)-thiomethyl]-3-cephem-4-carboxylic acid;

7-[β-cyano-ethylene(cis)-thio-acetamido]-3-[(tetrazolo[1,5-b]pyridazin-8-carboxymethyl-6-yl)-thiomethyl]-3-cephem-4-carboxylic acid.

EXAMPLE 7

To a solution of β-carboxamido-ethylene(cis)-thio-acetic acid (0.81 g) in acetonitrile/dimethylformamide (2:1; 60 ml), triethylamine (0.7 ml) and 2 drops of N-methylmorpholine were added. The mixture was cooled at $-5°$ C. and a solution of pivaloylchloride (0.61 ml) in anhydrous acetonitrile (10 ml) was added dropwise under stirring. After stirring for 30 minutes at $-5°$ C., a solution of 7-amino-3-[(1-ethyl-1,2,3,4-tetrazol-5-yl)-thiomethyl]-3-cephem-4-carboxylic acid (1.71 g) and triethylamine (0.7 ml) in acetonitrile/water (1:1; 70 ml) was added, maintaining the temperature at about 0° C. The mixture was stirred for 1 hour at 0° C., then for 2 hours at room temperature and evaporated to dryness; the residue was taken up with water and stratified with ethyl acetate and the pH was brought to 2.5 with 40% $H_3PO_4$.

After filtration of the residue and separation of ethyl acetate, the organic phase was washed with water, dried on $Na_2SO_4$ and evaporated to dryness under vacuum. The so obtained raw product was dissolved in methanol/acetone (1:1; 15 ml) and poured dropwise in ethyl ether (200 ml). After stirring for 2 hours and filtration, 7-[β-carboxamido-ethylene(cis)-thio-acetamido]-3-[(1-ethyl-1,2,3,4-tetrazol-5-yl)-thiomethyl]-3-cephem-4-carboxylic acid was obtained (1.21 g; yield 50%), m.p. 80°-83° C. (dec.).

Analysis: Found: C 39.79; H 4.26; N 19.88; S 20.03; $C_{18}H_{19}N_7O_5S_3$ requires: C 39.57; H 3.94; N 20.19; S 19.82.

U.V. (pH 7.4 buffer phosphate): $\lambda_{max}=274$ mμ; $E_1\,_{cm}1\%=415$

T.L.C.: $R_f=0.41$ ($CHCl_3:CH_3OH:H-COOH=160:20:20$);

I.R. (KBr): $\nu(C=O)$ β-lactam 1780 $cm^{-1}$; $\nu(C=O)$ acid 1660 $cm^{-1}$; $\nu(C-N)+\delta(N-H)$ sec. amide 1550 $cm^{-1}$.

β-carboxamido-ethylene(cis)-thio-acetic acid used as starting material was prepared as follows: to a solution of propiolamide (6.9 g) in water (20 ml) a solution of 70% thioglycolic acid (10 ml) in 20% NaOH (18.9 ml) was added under stirring at about 0° C. The solution was stirred again for 1 hour at 0° C. and then for 1 hour at room temperature. At the end of the stirring the solution was acidified under stirring with the stoichiometric amount of 70% perchloric acid. After cooling at about 5°-0° C., a solid precipitated which was filtered, taken up with water (45 ml), stirred for 10 minutes, filtered again and dried. 12.6 g of a mixture (9:1) of β-carboxamido-ethylene(cis)-thio-acetic acid and β-carboxamido-ethylene(trans)-thio-acetic acid were so obtained. The two acids have the same solubility in water and therefore by stirring the mixture with the suitable amount of water it is possible to dissolve all the trans-isomer, leaving still undissolved about 8/9 of the cis-isomer [the purification process can be controlled by thin layer chromatography (acetone/water/acetic acid 180:10:10)]: for instance, by means of three subsequent washings (twice with 50 ml of water and then with 100 ml of water) 10.9 g of the pure cis-isomer (yield 72%), m.p. 180°-181° C. were obtained;

Analysis: Found: C 37.22; H 4.37; N 8.66; S 20.00; $C_5H_7NO_3S$ requires: C 37.25; H 4.37; N 8.69; S 19.89.

I.R. (KBr): $\nu(N-H)$ —$NH_2$ group 3450,3210 $cm^{-1}$; $\nu(C=O)$ acid 1685 $cm^{-1}$; $\nu(C=O)$ amide 1625 $cm^{-1}$;

N.M.R. (DMSO-$d_6$): 3.43 δ(s, —S—$CH_2$—); 6.97 δ(d, =CH—S); 7.16 δ(d, —$CONH_2$); 12.00 δ(br-s OH); $J_{CH=CH(cis)}=10$ Hz.

EXAMPLE 8

By using the same method of example 7, the following compounds were prepared:

7-[β-carboxamido-ethylene(cis)-thio-acetamido]-3-[(1-carboxymethyl-1,2,3,4-tetrazol-5-yl)-thiomethyl]-3-cephem-4-carboxylic acid;

Analysis: Found: C 37.50; H 3.51; N 18.61; S 18.33; $C_{16}H_{17}N_7O_7S_3$ requires: C 37.30; H 3.32; N 19.00; S, 18.65.

U.V. (pH 7.4 buffer phosphate): $\lambda_{max}=275$ mμ; $E_1\,_{cm}1\%=399$

T.L.C.: $R_f=0.20$ ($CHCl_3:CH_3OH:H-COOH=160:70:30$)

I.R. (KBr): $\nu(C=O)$ β-lactam 1770 $cm^{-1}$; $\nu(C=O)$ sec. amide 1715 $cm^{-1}$; $\nu(C=O)$ prim. amide+$\nu(C=O)$ conjugated acid 1650 $cm^{-1}$; $\nu(C-N)+\delta(N-H)$ sec. amide 1550 $cm^{-1}$.

7-[β-carboxamido-ethylene(cis)-thio-acetamido]-3-[(1-β-carboxyethyl-1,2,3,4-tetrazol-5-yl)-thiomethyl]-3-cephem-4-carboxylic acid;

Analysis: Found: C 38.70; H 3.85; N 18.22; S 17.83. $C_{17}H_{19}N_7O_7S_3$ requires: C 38.56; H 3.61; N 18.51; S 18.16.

U.V. (pH 7.4 buffer phosphate): $\lambda_{max}=274$ mμ $E_1\,_{cm}1\%=365$

T.L.C.: $R_f=0.31$ ($CHCl_3:CH_3OH:H-COOH=160:70:30$)

I.R. (KBr): $\nu(C=O)$ β-lactam (1770 $cm^{-1}$; $\nu(C=O)$ sec. amide 1715 $cm^{-1}$; $\nu(C=O)$ prim. amide+$\nu(C=O)$ conjugated acid 1650 $cm^{-1}$; $\nu(C-N)+\delta(N-H)$ sec. amide 1550 $cm^{-1}$.

7-[β-carboxamido-ethylene(cis)-thio-acetamido]-3-[(1-β-carboxyethylene-1,2,3,4-tetrazol-5-yl)-thiomethyl]-3-cephem-4-carboxylic acid;

7-[β-carboxamido-ethylene(cis)-thio-acetamido]-3-[(1-β-sulfoethylene-1,2,3,4-tetrazol-5-yl)-thiomethyl]-3-cephem-4-carboxylic acid;

7-[β-caboxamido-ethylene(cis)-thio-acetamido]-3-[(1-(1)-propenyl-1,2,3,4-tetrazol-5-yl)-thiomethyl]-3-cephem-4-carboxylic acid.

EXAMPLE 9

To a solution of β-cyano-ethylene(cis)-thio-acetic acid (1.4 g) in anhydrous acetone (60 ml) and triethylamine (1.24 ml) cooled at $-10°$ C., isobutylchloroformate (1.7 ml) dissolved in anhydrous acetone (16 ml) was added under stirring. The stirring was continued for 30 minutes at $-10°$ C., then the mixture was cooled at $-30°$ C. A solution containing 7-amino-3-[(1-β-carboxyethyl-1,2,3,4-tetrazol-5-yl)-thiomethyl]-3-cephem-4-carboxylic acid (3.66 g) and triethylamine (4 ml) in 50% acetone (120 ml) was then added and the resulting mixture was stirred for 1 hour at a temperature between $-20°$ C. and $-30°$ C., subsequently for 1 hour at a temperatur between $-5°$ C. to 0° C. and afterwards for 3 hours at room temperature. The acetone was filtered and evaporated under vacuum; the residue was taken up with water (200 ml) and extracted with ethyl ether (2×100 ml). After separation the aqueous solution was brought to pH 2.5 with 10% hydrochloric acid and extracted with ethyl acetate. The organic phase was washed with water, dried on $Na_2SO_4$, concentrated to small volume and poured into cyclohexane so obtaining 7-[β-cyano-ethylene(cis)-thio-acetamido]-3-[1-(β-carboxy-ethyl-1,2,3,4-tetrazol-5-yl)-thiomethyl]-3-cephem-4-carboxylic acid; microanalysis, U.V., T.L.C., I.R. and N.M.R. data of this compound were identical to those already reported in example 2. By proceeding analogously, the following compounds were obtained: 7-(cyano-ethynylene-thio-acetamido)-3-[(1-carboxymethyl-1,2,3,4-tetrazol-5-yl)-thiomethyl]-3-cephem-4-carboxylic acid;

7-(cyano-ethynylene-thio-acetamido)-3-[(1-β-carboxyethyl-1,2,3,4-tetrazol-5-yl)-thiomethyl]-3-cephem-4-carboxylic acid;

7-(cyano-ethynylene-thio-acetamido)-3-[(1-sulfomethyl-1,2,3,4-tetrazol-5-yl)-thiomethyl]-3-cephem-4-carboxylic acid.

EXAMPLE 10

To a solution of 7-amino-3-[(tetrazolo[1,5-b]pyridazin-8-amino-6-yl)-thiomethyl]-3-cephem-4-carboxylic acid (3.80 g) and $NaHCO_3$ (2 g) in 50% aqueous acetone (60 ml), cooled at 0° C., a solution of 2.18 g of β-cyano-ethylene(cis)-thio-acetic acid chloride (obtained from the acid by reaction with oxalyl chloride in dimethylformamide at 0° C.) in acetone (30 ml) was added under stirring. The mixture was stirred for 20 minutes at a temperature between 0° C. and 5° C. The acetone was evaporated, ethyl acetate was added to the resulting aqueous solution which was then acidified with 8% hydrochloric acid to pH 2. The organic phase was washed with water, dried and evaporated under vacuum. The residue was treated with ethyl ether and filtered, so obtaining 7-[β-cyano-ethylene(cis)-thio-acetamido]-3-[(tetrazolo[1,5-b]pyridazin-8-amino-6-yl)-thiomethyl]-3-cephem-4-carboxylic acid (2.3 g), m.p. 170°–175° C. (dec.); microanalysis, U.V., T.L.C., I.R. and N.M.R. data of this compound were identical to those already reported in example 5.

By proceeding analogously, also the other compounds of the invention mentioned in the preceding examples were prepared.

EXAMPLE 11

To a solution containing 7-(bromo-acetamido)-3-[(1-ethyl-1,2,3,4-tetrazol-5-yl)-thiomethyl]-3-cephem-4-carboxylic acid (4.65 g) in $CH_2Cl_2$ (50 ml), triethylamine (2.8 ml) was added. After stirring for 30 minutes at room temperature, cis-1-cyano-2-mercapto-ethylene (0.85 g) was added and the mixture was stirred for 6 hours at room temperature. The obtained precipitate was filtered off; the organic solution was washed with water, dried and evaporated to dryness under vacuum. The residue was taken up with ethyl ether so obtaining 7-[β-cyano-ethylene(cis)-thio-acetamido]-3-[(1-ethyl-1,2,3,4-tetrazol-5-yl)-thiomethyl]-3-cephem-4-carboxylic acid (3.8 g), m.p. 80°–83° C. (dec.); microanalysis, U.V., T.L.C., I.R. and N.M.R. data of this compound were identical to those already reported in example I.

By proceeding analogously, also the other compounds of the invention mentioned in the preceding examples were obtained. 7-(bromo-acetamido)-3-[(1-ethyl-1,2,3,4-tetrazol-5-yl)-thiomethyl]-3-cephem-4-carboxylic acid used as starting material was prepared by reacting, using a known method, bromoacetylbromide with 7-amino-3-[(1-ethyl-1,2,3,4-tetrazol-5-yl)-thiomethyl]-3-cephem-4-carboxylic acid.

EXAMPLE 12

To a solution containing 7-(mercapto-acetamido)-3-[(1-ethyl-1,2,3,4-tetrazol-5-yl)-thiomethyl]-3-cephem-4-carboxylic acid (4.42 g) in $CH_2Cl_2$ (70 ml), triethylamine (2.8 ml) was added. The mixture was stirred for 30 minutes at room temperature and then cis-β-chloroacrylonitrile (0.87 g) dissolved in $CH_2Cl_2$ (15 ml) was added. After stirring for 4 hours at room temperature, the obtained precipitate was filtered off and the organic solution was washed with water, dried and evaporated to dryness under vacuum; the residue was taken up with ethyl ether, so obtaining 7-[β-cyano-ethylene(cis)-thio-acetamido]-3-[(1-ethyl-1,2,3,4-tetrazol-5-yl)-thiomethyl]-3-cephem-4-carboxylic acid (3.6 g), m.p. 80°–83° C. (dec.); microanalysis, U.V., T.L.C., I.R. and N.M.R. data of this compound were identical to those already reported in example 1.

By proceeding analogously, also the other compounds of the invention mentioned in the preceding examples were obtained.

EXAMPLE 13

To a solution containing β-carboxamido-thio-acetic acid(cis) (0.81 g) in acetonitrile/dimethylformamide 4:1 (50 ml), triethylamine (0.7 ml) and two drops of N-methylmorpholine were added. The solution was cooled at 0°–+5° C. and a solution of pivaloylchloride (0.61 ml) in acetonitrile (10 ml) was added dropwise. The mixture was stirred for 30 minutes at the same temperature, then a solution of 7-amino-3-[(tetrazolo[1,5-b]pyridazin-8-amino-6-yl)-thiomethyl]-3-cephem-4-carboxylic acid (1.9 g), triethylamine (0.5 ml) and $NaHCO_3$ (0.420 g) in acetonitrile/water 1:1 (80 ml) was added, maintaining the temperature at about 0° C. This mixture was stirred under cooling for 1 hour, then at room temperature for 2 hours, evaporated nearly to dryness and taken up again with water, stratified with ethyl acetate and the pH was brought to pH 2.5 with 40% $H_3PO_4$. The residue was filtered off and the ethyl acetate was separated; the organic phase was washed with water, dried on $Na_2SO_4$ and evaporated to dryness. The so obtained raw product was purified by re-precipitation pouring it into ethyl ether and they by stirring with acetone-methanol, so obtaining 7-[β-carboxamido-ethylene(cis)-thio-acetamido]-3-[(tetrazolo[1,5-b]pyridazin-8-amino-6-yl)-thiomethyl]-3-cephem-4-carboxylic acid (1.6 g; yield 60.5%), p.f. 165°–170° C. (dec.).

Analysis: Found: C 38.61; H 3.42; N 23.73; S 18.10; $C_{17}H_{17}N_9O_5S_3$ requires: C 39.00; H 3.28; N 24.1; S 18.40.

U.V. (pH 7.4 buffer phosphate): $\lambda_{max}=271$ mμ $E_1$ $cm^{1\%}=580$

T.L.C.: $R_f=0.29$ ($CHCl_3:CH_3OH:HCOOH=160:40:20$)

I.R. (KBr): ν(N-H) -$NH_2$ group 3380, 3280, 3160 $cm^{-1}$; ν(C=O) β-lactam 1765 $cm^{-1}$; ν(C=O) conjugated amide 1660 $cm^{-1}$; ν(-$NH_2$) on heterocycle 1570 $cm^{-1}$; ν(C-N)+δ(N-H) sec. aide 1570-1530 $cm^{-1}$.

N.M.R. ppm (DMSO-$d_6$); 3.68 (2H, q, 2-$CH_2$—); 3.73 (2H, s, —S—$CH_2$—CO—); 4.31 (2H, q, 3—$CH_2$); 5.10 (1H, d, 6-H); 5.63 (1H, d-d, 7-H); 5.94 (1H, d, —CO—CH=); 6.39 (1H, s, 7-H on the pyridazine ring); 6.97 (1H, d, =CH—S) $J_{CH=CH(cis)}=10$ Hz; 7.16 (2H, d, —$CONH_2$); 7.98 (2H, br-s, 8-$NH_2$ on the pyridazine ring); 9.2 (1H, d, —CONH).

EXAMPLE 14

By using the same method of example 13, the following compounds were prepared:

7-[β-carboxamido-ethylene(cis)-thio-acetamido]-3-[(tetrazolo[1,5-b]pyridazin-6-yl)-thiomethyl]-3-cephem-4-carboxylic acid;

Analysis: Found: C 39.81; H 3.21; N 21.81; S 18.44; $C_{17}H_{16}N_8O_5S_3$ requires: C 40.10; H 3.17; N 22.10; S 18.90.

U.V. (pH 7.4 buffer phosphate): $\lambda_{max}=271$ mμ $E_{1\ cm}^{1\%}=461$, shoulder at 242 mμ, $E_{1\ cm}^{1\%}=450$ T.L.C.: $R_f=0.26$ (CHCl$_3$:CH$_3$OH:HCOOH=160:40:20)

I.R. (KBr) ν(C=O) β-lactam 1780 cm$^{-1}$; ν(C=O) prim. amide 1660 cm$^{-1}$; ν(C-N)+δ(N-H) sec. amide 1550 cm$^{-1}$;

7-[β-carboxamido-ethylene(cis)-thio-acetamido]-3-[(tetrazolo[1,5-b]pyridazin-7-amino-S-yl)-thiomethyl]-3-cephem-4-carboxylic acid;

7-[β-cyano-ethylene(cis)-thio-acetamido]-3-[(tetrazolo[1,5-b]pyridazin-7,8-diamino-6-yl)-thiomethyl]-3-cephem-4-carboxylic acid;

7-[β-carboxamido-ethylene(cis)-thio-acetamido]-3-[(tetrazolo[1,5-b]pyridazin-7,8-diamino-6-yl)-thiomethyl]-3-cephem-4-carboxylic acid;

7-(cyano-ethynylene-thio-acetamido)-3-[(tetrazolo[1,5-b]pyridazin-6-yl)-thiomethyl]-3-cephem-4-carboxylic acid;

7-(cyano-ethynylene-thio-acetamido)-3-[(tetrazolo[1,5-b]pyridazin-8-amino-6-yl)-thiomethyl]-3-cephem-4-carboxylic acid;

7-(carboxamido-ethynylene-thio-acetamido)-3-[(tetrazolo[1,5-b]pyridazin-6-yl)-thiomethyl]-3-cephem-4-carboxylic acid;

7-(carboxamido-ethynylene-thio-acetamido)-3-[(tetrazolo[1,5-b]pyridazin-8-amino-6-yl)-thiomethyl]-3-cephem-4-carboxylic acid;

7-[β-carboxy-ethylene(cis)-thio-acetamido]-3-[(tetrazolo[1,5-b]pyridazin-6-yl)-thiomethyl]-3-cephem-4-carboxylic acid;

U.V. (pH 7.4 buffer phosphate) $\lambda_{max}=270$ mμ; $E_{1\ cm}^{1\%}=590$

T.L.C.: $R_f=0.30$ (CHCl$_3$:CH$_3$OH:HCOOH=160:40:20);

7-[β-carboxy-ethylene(cis)-thio-acetamido]-3-[(tetrazolo[1,5-b]pyridazin-8-amino-6-yl)-thiomethyl]-3-cephem-4-carboxylic acid;

U.V. (pH 7.4 buffer phosphate) $\lambda_{max}=271$ mμ; $E_{1\ cm}^{1\%}=570$

T.L.C.: $R_f=0.20$ (CHCl$_3$:CH$_3$OH:HCOOH=160:40:20).

EXAMPLE 15

To a solution containing the sodium salt of the 7-[β-cyano-ethylene(cis)-thio-acetamido]-cephalosporanic acid (4.19 g) in acetone (40 ml) and buffer phosphate (pH 7) (200 ml), 6-mercapto-8-amino-tetrazolo[1,5-b]pyridazin (1.9 g) and NaHCO$_3$ (1.84 g) were added and the mixture was stirred for 6 hours at 60° C. then it is cooled, stratified with ethyl acetate and acidified with 10% HCl until the pH was brought to 2. The two phases system was filtered, the organic phase was separated; the aqueous phase was brought to pH 4.5 with 10% NH$_3$ and extracted with ethyl acetate.

The organic phase was washed with water, dried on and evaporated to dryness so obtaining 7-[β-cyano-ethylene(cis)-thio-acetamido]-3-[(tetrazolo[1,5-b]pyridazin-8-amino-6-yl)-thiomethyl]-3-cephem-4-carboxylic acid (yield 65%); microanalysis, U.V., T.L.C., I.R. and N.M.R. data of this compound were identical to those already reported in example 5.

By proceeding analogously, also the other compounds of the invention mentioned in the preceding examples were prepared.

EXAMPLE 16

To a solution of β-cyano-ethylene(cis)-thio-acetic acid (1.44 g) in anhydrous tetrahydrofuran (50 ml), dicyclohexylcarbodiimide (2.1 g) was added and the mixture was stirred for 30 minutes at room temperature. To this mixture, a solution of 7-amino-3-[(tetrazolo[1,5-b]pyridazin-8-amino-6-yl)-thiomethyl]-3-cephem-4-carboxylic acid (3.8 g) and NaHCO$_3$ (0.84 g) in tetrahydrofuran/water (1:1; 60 ml) was added. After stirring for 3 hours at room temperature the tetrahydrofuran was evaporated under vacuum; the residue was taken up with water and the dicyclohexyl-urea was filtered off.

The filtrate was stratified with ethyl acetate, acidified with 20% H$_2$SO$_4$ to pH 2.5; the organic layer was separated, washed with water, evaporated to small volume and then ethyl ether was added to give a solid which was filtered and then stirred with ethyl ether so obtaining 7-[β-cyano-ethylene(cis)-thio-acetamido]-3-[(tetrazolo[1,5-b]pyridazin-8-amino-6-yl)-thiomethyl]-3-cephem-4-carboxylic acid, m.p. 170°–175° C. (dec.); microanalysis, U.V., T.L.C., I.R. and N.M.R. data were identical to those already reported in example 5.

By proceeding analogously, also the other compounds of the invention mentioned in the preceding examples were obtained.

EXAMPLE 17

To an aqueous suspension of 7-[β-carboxamido-ethylene(cis)-thio-acetamido]-3-[(tetrazolo[1,5-b]pyridazin-8-amino-6-yl)-thiomethyl]-3-cephem-4-carboxylic acid (5.23 g) in water (80 ml), the stoichiometric amount of NaHCO$_3$ was added, so obtaining the complete solution of the compound. This solution was then lyophilized so obtaining sodium salt of 7-[β-carboxamido-ethylene(cis)-thio-acetamido]-3-[(tetrazolo[1,5-b]pyridazin-8-amino-6-yl)-thiomethyl]-3-cephem-4-carboxylic acid.

Analogously, the salts of the compounds described in the preceding examples were prepared.

EXAMPLE 18

To a solution of 7-[β-carboxamido-ethylene(cis)-thio-acetamido]-3-[(1-tetrazolo[1,5-b]pyridazin-8-amino-6-yl)-thiomethyl]-3-cephem-4-carboxylic acid (1.3 g) in ethyl acetate (30 ml), the stoichiometric amount of a 30% solution of sodium 2-ethyl-hexanoate in isopropyl alcohol was added. After stirring for 30 minutes at room temperature, the mixture was diluted with petroleum ether and the obtained precipitate was filtered to give sodium salt of 7-[β-carboxamido-ethylene(cis)-thio-acetamido]-3-[(tetrazolo[1,5-b]pyridazin-8-amino-6-yl)-thiomethyl]-3-cephem-4-carboxylic acid.

Analogously, the salts of the compounds described in the preceding examples were prepared.

EXAMPLE 19

To a solution containing β-cyano-ethylene(trans)-thio-acetic acid (2.88 g) and triethylamine (2.8 g) in anhydrous acetone (160 ml) some drops of N-methylmorpholine were added. The mixture was cooled at −10° C. and then pivaloylchloride (2.44 ml) dissolved in anhydrous acetone (40 ml) was added under stirring and then, after stirring for 30 minutes at −10° C., a solution containing 7-amino-3-[(1-β-carboxyethyl-1,2,3,4-tetrazol-5-yl)-thiomethyl]-3-cephem-4-carboxylic acid (7.72 g) and triethylamine (5.6 ml) in 50% acetone (320 ml), cooled at 0° C., was added after 30 minutes.

The mixture was then stirred at 0° C. for 1 hour and afterwards at room temperature for 3 hours. The acetone was evaporated under vacuum. The residue was taken up with water, stratified with ethyl acetate and the pH of the mixture was brought to 2.5 with 40% $H_3PO_4$.

After filtration, the ethyl acetate was separated and the organic phase was washed with water, dried on $Na_2SO_4$ and evaporated to small volume. Ethyl ether was added to give a solid, which was filtered and stirred with ethyl ether. The solid was filtered again so obtaining 5.1 g (yield 50%) of 7-[β-cyano-ethylene(trans)-thio-acetamido]-3-[(1-β-carboxyethyl-1,2,3,4-tetrazol-5-yl)-thiomethyl]-3-cephem-4-carboxylic acid, m.p. 108°–110° C. (dec.);

Analysis: Found: C 40.20; H 3.42; N 19.21; S 18.10; $C_{17}H_{17}N_7O_6S_3$ requires: C 39.91; H 3.35; N 19.17; S 18.80.

U.V. (pH 7.4 buffer phosphate): $\lambda_{max} = 267$ mμ; $E_1^{cm\,1\%} = 385$

T.L.C.: $R_f = 0.50$ ($CHCl_3:CH_3OH:HCOOH = 160:40:20$)

I.R. (KBr): ν(C≡N) conjugated 2205 cm$^{-1}$; ν(C=O) β-lactam 1770 cm$^{-1}$; ν(C=) acid 1720 cm$^{-1}$; ν(C-N)+δ(N-H) sec. amide 1530 cm$^{-1}$.

N.M.R. ppm (DMSO-d$_6$): 2.93 (2H, t, —CH$_2$—COOH on tetrazole ring); 3.83 (4H, br-s, —S—CH$_2$CO— and 2-CH$_2$); 4.4 (4H, m, >N-CH$_2$— and 3-CH$_2$); 5.08 (1H, d, 6-H); 5.69 (1H, d-d, 7-H); 5.72 (1H, d, NC-CH=); 7.66 (1H, d, =CH—S—) $J_{CH=CH(trans)} = 16$ Hz; 9.2 (1H, d, —CO—NH).

EXAMPLE 20

By using the same method of example 19 and reacting β-cyano-ethylene(trans)-thio-acetic acid, the (trans)-isomers of the compounds reported in examples 1, 3, 4, 5 and 6 were obtained. β-cyano-ethylene(trans)-thio-acetic acid used as starting material was prepared according to the following methods:

(method A)—to a solution of 70% thioglycolic acid (2.1 ml) and triethylamine (5.6 ml) in water (50 ml), cooled at +5° C., a solution of trans-β-chloroacrylonitrile (1.73 g) in tetrahydrofuran (7 ml) was added dropwise. The mixture was stirred for 30 minutes at room temperature, acidified with 20% $H_2SO_4$. The obtained precipitate was extracted with ethyl acetate; the extracts were washed with a saturated solution of NaCl, dried on $Na_2SO_4$, treated with charcoal and evaporated so obtaining an oil which solidifies to give β-cyano-ethylene(trans)-thio-acetic acid (2.5 g; yield 88%), m.p. = 81°–86° C.;

Analysis: Found: C 41.81; H 3.57; N 9.71; S 22.31; $C_5H_5NO_2S$ requires C 41.94; H 3.52; N 9.78; S 22.39.

I.R. (KBr): ν(C≡N) conjugated 2220 cm$^{-1}$; ν(C=O) acid 1720 cm$^{-1}$; ν(C=C) conjugated 1575 cm$^{-1}$; ν(C-H):C=C trans 930 cm$^{-1}$.

N.M.R. (DMSO-d$_6$): 5.56 δ(d,NC-CH=), 7.78 δ(d, =CH-S); $J_{CH=CH}(trans) = 16$ Hz;

(method B)—to a solution of 70% thioglycolic acid (0.5 ml) and NaHCO$_3$ (0.84 mg) in water (50 ml), β-tosyl-acrylonitrile (1.03 g) was added under stirring. The mixture was stirred for 3 hours at room temperature and filtered. The solution was acidified with 20% $H_2SO_4$ and extracted with ethyl acetate. The organic phase was dried on $Na_2SO_4$ and evaporated to dryness so obtaining β-cyano-ethylene(trans)-thio-acetic acid (0.65 g; yield 91%). By purification through the formation of dicyclohexylamine salt a product identical to that prepared according to method A was obtained. β-tosyl-acrylonitrile used as starting material was prepared by reacting sodium salt of p-toluenesulphinic acid and β-chloro-acrylonitrile in a mixture of dioxane, water and boric acid according to a known method.

EXAMPLE 21

To a suspension of sodium salt of 7-[β-carboxamido-ethylene(cis)-thio-acetamido]-3-[(tetrazolo[1,5-b]pyridazin-8-amino-6-yl)-thiomethyl]-3-cephem-4-carboxylic acid (2.74 g) in acetone (40 ml), a 10% solution of sodium iodide in water (0.4 ml) and chloromethyl-pivalate (0.72 ml) was added. The suspension was heated for 3 hours under reflux and after cooling at 5° C., the solid was filtered off and the resulting solution evaporated under vacuum. The oily residue was dissolved in ethyl acetate (50 ml), the resulting solution washed with a 5% solution of NaHCO$_3$ in water and then with water, dried and evaporated to dryness so obtaining the pivaloyloxymethyl ester of 7-[β-carboxamido-ethylene(cis)-thio-acetamido]-3-[(tetrazolo[1,5-b]pyridazin-8-amino-6-yl)-thiomethyl]-3-cephem-4-carboxylic acid.

Analogously, the pivaloyloxymethyl esters of the compounds described in the preceding examples were obtained.

EXAMPLE 22

An injectable pharmaceutical composition was performed by dissolving 100–500 mg of sodium 7-[β-carboxamido-ethylene(cis)-thio-acetamido]-3-[(tetrazolo[1,5-b]pyridazin-8-amino)-6-yl)-thiomethyl]-3-cephem-4-carboxylate in sterile water or steril normal saline solution (1–2 ml).

Analogously, injectable pharmaceutical compositions containing the compounds previously described in the preceding examples were prepared.

We claim:

1. A compound of the formula

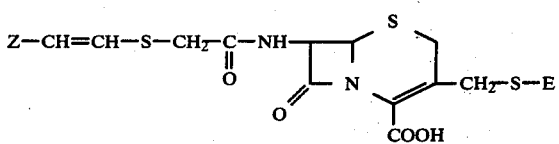

wherein
E is

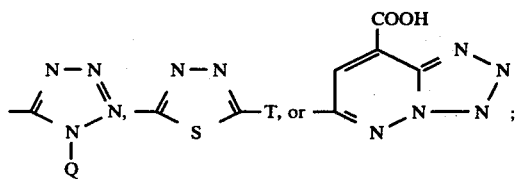

Q is —C$_2$H$_5$,—CH$_2$—CH=CH$_2$,—CH=CH—CH$_3$, or

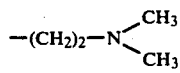

T is amino or —CH$_2$COOH, and
Z is cyano, or, when E is

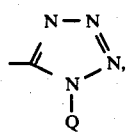

Z is cyano or carbamoyl, and the pharmaceutically or veterinarily acceptable salts thereof.

2. A compound of claim 1, said compound of formula

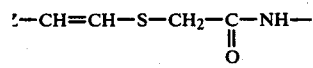

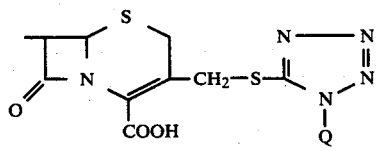

wherein

Z is cyano or carbamoyl;
Q is —C$_2$H$_5$, —CH$_2$—CH=CH$_2$, —CH=CH—CH$_3$ or

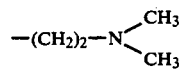

and the pharmaceutically or veterinarily acceptable salts thereof.

3. A compound as claimed in claim 2 wherein said compound is selected from the group consisting of:
7-[β-cyano-ethylene(cis)-thio-acetamido]-3-[(1-ethyl-1,2,3,4-tetrazol-5-yl)-thiomethyl]-3-cephem-4-carboxylic acid;
7-[β-cyano-ethylene(cis)-thio-acetamido]-3-[(1-(2)-propenyl-1,2,3,4-tetrazol-5-yl)-thiomethyl]-3-cephem-4-carboxylic acid;
7-[β-cyano-ethylene(cis)-thio-acetamido]-3-[(1-(1)-propenyl-1,2,3,4-tetrazol-5-yl)-thiomethyl]-3-cephem-4-carboxylic acid;
7-[β-cyano-ethylene(cis)-thio-acetamido]-3-[(1-β-dimethylaminoethyl-1,2,3,4-tetrazol-5-yl)-thiomethyl]-3-cephem-4-carboxylic acid;
7-[β-carboxamido-ethylene(cis)-thio-acetamido]-3-[(1-ethyl-1,2,3,4-tetrazol-5-yl)-thiomethyl]-3-cephem-4-carboxylic acid,
and the pharmaceutically or veterinarily acceptable salts thereof.

4. A compound of claim 1, said compound of formula

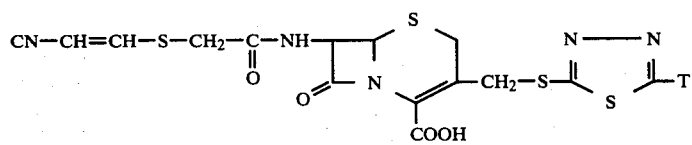

wherein
T is amino or —CH$_2$COOH,
and the pharmaceutically or veterinarily acceptable salts thereof.

5. A compound as claimed in claim 4 wherein said compound is selected from the group consisting of:
7-[β-cyano-ethylene(cis)-thio-acetamido]-3-[(5-amino-1,3,4-thiadiazol-2-yl)-thiomethyl]-3-cephem-4-carboxylic acid;
7-[β-cyano-ethylene(cis)-thio-acetamido]-3-[(5-carboxymethyl-1,3,4-thiadiazol-2-yl)-thiomethyl]-3-cephem-4-carboxylic acid,
and the pharmaceutically or veterinarily acceptable salts thereof.

6. A compound of claim 1, said compound of formula

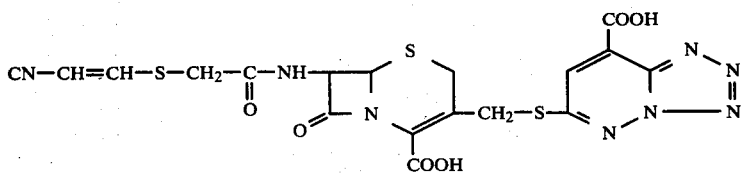

and the pharmaceutically or veterinarily acceptable salts thereof.

7. A pharmaceutical or veterinary composition suitable for the treatment of infections caused by Gram-positive and Gram-negative microorganisms, said composition consisting essentially of a therapeutically effective amount of a compound according to any one of claims 1, 2, 3, 4, 5 or 6, and a pharmaceutically or veterinarily acceptable carrier or diluent.

8. Method for the treatment of an infection caused by Gram-positive or Gram-negative microorganisms in a patient, said method comprising administering to said patient a therapeutically effective amount of a compound of any one of claims 1, 2, 3, 4, 5 or 6.

9. Method of claim 8 wherein said compound is administered orally or parenterally.

* * * * *